US008876795B2

(12) United States Patent
Fiering et al.

(10) Patent No.: US 8,876,795 B2
(45) Date of Patent: Nov. 4, 2014

(54) DRUG DELIVERY APPARATUS

(75) Inventors: Jason O. Fiering, Boston, MA (US);
Mark J. Mescher, West Newton, MA (US); Erin E. Pararas, Swampscott, MA (US); Jeffrey T. Borenstein, Newton, MA (US); William F. Sewell, Sherborn, MA (US); Sharon G. Kujawa, Bedford, MA (US); Michael J. McKenna, Southborough, MA (US); Ernest S. Kim, Cambridge, MA (US)

(73) Assignees: The Charles Stark Draper Laboratory, Inc., Cambridge, MA (US); Massachusetts Eye and Ear Infirmary, Boston, MA (US)

( * ) Notice: Subject to any disclaimer, the term of this patent is extended or adjusted under 35 U.S.C. 154(b) by 50 days.

(21) Appl. No.: 13/364,583

(22) Filed: Feb. 2, 2012

(65) Prior Publication Data
US 2013/0053823 A1 Feb. 28, 2013

Related U.S. Application Data

(60) Provisional application No. 61/438,934, filed on Feb. 2, 2011.

(51) Int. Cl.
*A61M 31/00* (2006.01)
*A61M 5/142* (2006.01)

(52) U.S. Cl.
CPC ... *A61M 5/14276* (2013.01); *A61M 2210/0668* (2013.01)
USPC .......................................... 604/514

(58) Field of Classification Search
USPC ......................... 604/514, 247, 151, 264, 246
See application file for complete search history.

(56) References Cited

U.S. PATENT DOCUMENTS

| 3,386,469 | A | | 6/1968 | Kelly |
| 4,013,074 | A | | 3/1977 | Siposs |
| 4,034,759 | A | * | 7/1977 | Haerr ............................. 604/514 |
| 4,152,098 | A | | 5/1979 | Moody et al. |
| 4,181,245 | A | | 1/1980 | Garrett et al. |
| 4,487,603 | A | | 12/1984 | Harris |
| 4,505,710 | A | * | 3/1985 | Collins ........................ 604/891.1 |

(Continued)

FOREIGN PATENT DOCUMENTS

| AU | 2010203141 A1 | 8/2010 |
| EP | 1 331 019 A2 | 7/2003 |

(Continued)

OTHER PUBLICATIONS

Brown et al. "Osmotic pump implant for chronic infusion of drugs into the inner ear", Hearing Research 70, 1993, pp. 167-172.

(Continued)

*Primary Examiner* — Aarti B Berdichevsky
(74) *Attorney, Agent, or Firm* — Foley & Lardner LLP; Edward A. Gordon

(57) ABSTRACT

An implantable drug delivery apparatus for delivering a drug into a bodily fluid in a bodily cavity of a patient over a period of time includes a drug supply reservoir to supply drug into a delivery channel and an actuator for delivering the drug to a predetermined location in the bodily cavity of the patient, such as, for example, a cochlea of a human ear. The drug is loaded into the delivery channel while producing substantially negligible flow at an outlet of the delivery channel.

31 Claims, 12 Drawing Sheets

(56) References Cited

U.S. PATENT DOCUMENTS

| | | |
|---|---|---|
| 4,541,429 A | 9/1985 | Prosl et al. |
| 4,594,058 A | 6/1986 | Fischell |
| 4,594,059 A | 6/1986 | Becker |
| 4,604,090 A | 8/1986 | Reinicke |
| 4,634,427 A | 1/1987 | Hannula et al. |
| 4,824,073 A | 4/1989 | Zdeblick |
| 4,858,883 A | 8/1989 | Webster |
| 4,944,487 A | 7/1990 | Holtermann |
| 5,065,978 A | 11/1991 | Albarda et al. |
| 5,205,819 A | 4/1993 | Ross et al. |
| 5,441,597 A | 8/1995 | Bonne et al. |
| 5,476,446 A | 12/1995 | Arenburg |
| 5,499,979 A | 3/1996 | Wong et al. |
| 5,542,821 A | 8/1996 | Dugan |
| 5,578,002 A | 11/1996 | Slettenmark |
| 5,593,130 A | 1/1997 | Hansson et al. |
| 5,643,207 A * | 7/1997 | Rise .......................... 604/93.01 |
| 5,665,070 A | 9/1997 | McPhee |
| 5,725,363 A | 3/1998 | Bustgens et al. |
| 5,750,015 A | 5/1998 | Soane et al. |
| 5,759,014 A | 6/1998 | VanLintel |
| 5,770,029 A | 6/1998 | Nelson et al. |
| 5,779,868 A | 7/1998 | Parce et al. |
| 5,839,467 A | 11/1998 | Saaski et al. |
| 5,858,188 A | 1/1999 | Soane et al. |
| 5,858,195 A | 1/1999 | Ramsey |
| 5,880,071 A | 3/1999 | Parce et al. |
| 5,895,372 A * | 4/1999 | Zenner et al. .............. 604/93.01 |
| 5,938,904 A | 8/1999 | Bader et al. |
| 5,958,203 A | 9/1999 | Parce et al. |
| 5,962,081 A | 10/1999 | Ohman et al. |
| 5,971,355 A | 10/1999 | Biegelsen et al. |
| 5,972,187 A | 10/1999 | Parce et al. |
| 5,989,399 A | 11/1999 | Chu et al. |
| 5,989,402 A | 11/1999 | Chow et al. |
| 5,993,634 A | 11/1999 | Simpson et al. |
| 6,001,229 A | 12/1999 | Ramsey |
| 6,007,690 A | 12/1999 | Nelson et al. |
| 6,010,607 A | 1/2000 | Ramsey |
| 6,010,608 A | 1/2000 | Ramsey |
| 6,017,434 A | 1/2000 | Simpson et al. |
| 6,033,191 A | 3/2000 | Kamper et al. |
| 6,033,546 A | 3/2000 | Ramsey |
| 6,033,628 A | 3/2000 | Kaltenbach et al. |
| 6,042,709 A | 3/2000 | Parce et al. |
| 6,042,710 A | 3/2000 | Dubrow |
| 6,056,727 A | 5/2000 | O'Neil |
| 6,068,010 A | 5/2000 | Reinicke |
| 6,068,752 A | 5/2000 | Dubrow et al. |
| 6,080,295 A | 6/2000 | Parce et al. |
| 6,086,825 A | 7/2000 | Sundberg et al. |
| 6,087,743 A | 7/2000 | Guckel et al. |
| 6,093,296 A | 7/2000 | Soane et al. |
| 6,103,199 A | 8/2000 | Bjornson et al. |
| 6,110,343 A | 8/2000 | Ramsey et al. |
| 6,113,768 A | 9/2000 | Fuhr et al. |
| 6,120,666 A | 9/2000 | Jacobson et al. |
| 6,123,316 A | 9/2000 | Biegelsen et al. |
| 6,126,140 A | 10/2000 | Johnson et al. |
| 6,126,804 A | 10/2000 | Andresen |
| 6,132,579 A | 10/2000 | Edwards et al. |
| 6,136,171 A | 10/2000 | Frazier et al. |
| 6,153,073 A | 11/2000 | Dubrow et al. |
| 6,176,991 B1 | 1/2001 | Nordman |
| 6,193,866 B1 | 2/2001 | Bader et al. |
| 6,198,966 B1 | 3/2001 | Heruth |
| 6,207,031 B1 | 3/2001 | Adourian et al. |
| 6,227,809 B1 | 5/2001 | Forster et al. |
| 6,231,737 B1 | 5/2001 | Ramsey et al. |
| 6,235,175 B1 | 5/2001 | Dubrow et al. |
| 6,251,247 B1 | 6/2001 | Mitsuhashi et al. |
| 6,254,754 B1 | 7/2001 | Ross et al. |
| 6,261,430 B1 | 7/2001 | Yager et al. |
| 6,261,431 B1 | 7/2001 | Mathies et al. |
| 6,264,892 B1 | 7/2001 | Kaltenbach et al. |
| 6,280,148 B1 | 8/2001 | Zengerle et al. |
| 6,284,113 B1 | 9/2001 | Bjornson et al. |
| 6,287,520 B1 | 9/2001 | Parce et al. |
| 6,296,749 B1 | 10/2001 | Balch et al. |
| 6,296,752 B1 | 10/2001 | McBride et al. |
| 6,306,272 B1 | 10/2001 | Soane et al. |
| 6,306,273 B1 | 10/2001 | Wainright et al. |
| 6,341,758 B1 | 1/2002 | Shih et al. |
| 6,342,142 B1 | 1/2002 | Ramsey |
| 6,375,817 B1 | 4/2002 | Taylor et al. |
| 6,386,780 B1 | 5/2002 | Brummernhenrich |
| 6,406,605 B1 | 6/2002 | Moles |
| 6,413,400 B1 | 7/2002 | Soane et al. |
| 6,423,198 B1 | 7/2002 | Manz et al. |
| 6,440,102 B1 | 8/2002 | Arenberg et al. |
| 6,440,284 B1 | 8/2002 | Dubrow |
| 6,448,090 B1 | 9/2002 | McBride |
| 6,458,259 B1 | 10/2002 | Parce et al. |
| 6,482,177 B1 | 11/2002 | Leinders |
| 6,485,625 B1 | 11/2002 | Simpson et al. |
| 6,527,003 B1 | 3/2003 | Webster |
| 6,540,895 B1 | 4/2003 | Spence et al. |
| 6,547,942 B1 | 4/2003 | Parce et al. |
| 6,561,224 B1 | 5/2003 | Cho |
| 6,561,997 B1 * | 5/2003 | Weitzel et al. ............... 604/6.09 |
| 6,572,830 B1 | 6/2003 | Burdon et al. |
| 6,582,576 B1 | 6/2003 | Chow et al. |
| 6,592,733 B1 | 7/2003 | Foley et al. |
| 6,635,226 B1 | 10/2003 | Tso et al. |
| 6,659,982 B2 | 12/2003 | Douglas et al. |
| 6,660,147 B1 | 12/2003 | Woudenberg et al. |
| 6,685,697 B1 * | 2/2004 | Arenberg et al. .......... 604/890.1 |
| 6,752,376 B1 | 6/2004 | Satou et al. |
| 6,752,914 B1 | 6/2004 | Hassard |
| 6,764,060 B2 | 7/2004 | Fukano et al. |
| 6,773,567 B1 | 8/2004 | Wolk |
| 6,808,609 B1 | 10/2004 | Soane et al. |
| 6,824,663 B1 | 11/2004 | Boone |
| 6,827,831 B1 | 12/2004 | Chow et al. |
| 6,929,030 B2 | 8/2005 | Unger et al. |
| 6,929,239 B1 | 8/2005 | Colin et al. |
| 6,945,116 B2 | 9/2005 | Xie et al. |
| 6,948,918 B2 | 9/2005 | Hansen |
| 6,986,365 B2 | 1/2006 | Henning et al. |
| 7,033,148 B2 | 4/2006 | Bunner et al. |
| 7,134,639 B2 | 11/2006 | Gilbert et al. |
| 7,147,205 B1 | 12/2006 | Fischer et al. |
| 7,192,001 B2 | 3/2007 | Wise et al. |
| 7,232,109 B2 | 6/2007 | Driggs et al. |
| 7,254,008 B2 | 8/2007 | Xie et al. |
| 7,293,581 B2 | 11/2007 | Gilbert et al. |
| 7,311,503 B2 | 12/2007 | Van Lintel et al. |
| 7,867,193 B2 | 1/2011 | McKenna et al. |
| 7,867,194 B2 | 1/2011 | Fiering et al. |
| 2002/0048536 A1 | 4/2002 | Bergh et al. |
| 2002/0098097 A1 | 7/2002 | Singh |
| 2002/0127736 A1 | 9/2002 | Chou et al. |
| 2002/0144738 A1 | 10/2002 | Unger et al. |
| 2002/0166585 A1 | 11/2002 | O'Connor et al. |
| 2002/0172969 A1 | 11/2002 | Burns et al. |
| 2003/0071235 A1 | 4/2003 | Gamble et al. |
| 2003/0127329 A1 | 7/2003 | DeVoe et al. |
| 2003/0171738 A1 | 9/2003 | Konieczynski et al. |
| 2003/0175947 A1 | 9/2003 | Liu et al. |
| 2003/0196695 A1 | 10/2003 | O'Connor et al. |
| 2003/0229336 A1 | 12/2003 | Jacobsen et al. |
| 2004/0026461 A1 | 2/2004 | Bougamont et al. |
| 2004/0036047 A1 | 2/2004 | Richter |
| 2004/0053290 A1 | 3/2004 | Terbrueggen et al. |
| 2004/0089357 A1 | 5/2004 | Dube et al. |
| 2004/0127852 A1 | 7/2004 | Gray et al. |
| 2004/0188648 A1 | 9/2004 | Xie et al. |
| 2004/0249363 A1 | 12/2004 | Burke et al. |
| 2005/0065584 A1 | 3/2005 | Schiff et al. |
| 2005/0072946 A1 | 4/2005 | Studer et al. |
| 2005/0116798 A1 | 6/2005 | Bintoro et al. |
| 2005/0131332 A1 | 6/2005 | Kelly et al. |
| 2005/0238506 A1 * | 10/2005 | Mescher et al. ........... 417/413.1 |
| 2006/0030837 A1 | 2/2006 | McKenna et al. |

(56) References Cited

U.S. PATENT DOCUMENTS

| | | | |
|---|---|---|---|
| 2006/0287689 | A1 | 12/2006 | Debruyne et al. |
| 2007/0200081 | A1 | 8/2007 | Elizarov et al. |
| 2007/0234785 | A1 | 10/2007 | Beerling et al. |
| 2008/0009836 | A1 | 1/2008 | Fiering et al. |
| 2008/0249510 | A1 | 10/2008 | Mescher et al. |
| 2010/0030130 | A1* | 2/2010 | Parker et al. .................. 604/21 |

FOREIGN PATENT DOCUMENTS

| | | |
|---|---|---|
| WO | WO-95/20409 | 8/1995 |
| WO | WO-99/38552 | 8/1999 |
| WO | WO-02/11703 | 2/2002 |
| WO | WO-03/034960 | 5/2003 |
| WO | WO-03/075984 | 9/2003 |
| WO | WO-03/099351 | 12/2003 |
| WO | WO-2005/072793 | 8/2005 |
| WO | WO-2006/068263 | 6/2006 |
| WO | WO-2007/024829 | 3/2007 |

OTHER PUBLICATIONS

Cabuz et al. "MEMS-Based Flow Controller for Flow Cytometry" DARPA Contract MDA972-00-C-0029, 2002, 2 pgs.

Carvalho et al. "The Effect of Cochlesostomy and Intracochlear Infuction on Auditory Brain Stem Response Threshold in the Guinea Pig," The American Journal of Otology, 20, pp. 87-90 1999.

Charabi, Samih. "Round Window Gentamicin μ-Catheter—a New Therapeutic Tool in Ménière's Disease." Acta Oto-Laryngologica 120.539 (2000): 108-110.

Cousseau et al. "Improved Micro-Flow Regulator for Drug Delivery Systems," IEEE, 2001, pp. 527-530.

Dube et al. "26.1: A Si-Based FPW Sensor Array System with Polymer Microfluidics Integrated on a PCB," IEEE, 2002, pp. 460-465.

Fitch et al. "Pressure-Based Mass Flow Control Using Thermopneumatically-Actuated Microvalves," In Proceedings, Sensors and Actuators Workshop, pp. 162-165, Transducers Research Foundation, Cleveland, OH, 1998.

Gantz et al. "Combining Acoustic and Electric Hearing," Department of Otolaryngology-Head and Neck Surgery and Department of Speech and Pathology, University of Iowa, 2003, pp. 118.

Hoffer et al. "Microdose Gentamicin Administration via the Round Window Microcatheter Results in Patients with Meniere's Disease," Annals New York Academy of Sciences, 2001, pp. 46-51.

International Preliminary Report on Patentability and Written Opinion issued Aug. 15, 2013 in PCT Application No. PCT/US2012/023598.

International Search Report and Written Opinion for Application No. PCT/US05/002727, 10 pages, dated Apr. 28, 2005.

International Search Report and Written Opinion for Application No. PCT/US07/017817, 10 pages, dated Jan. 18, 2008.

International Search Report and Written Opinion for Application No. PCT/US08/001324, 16 pages, dated Sep. 30, 2008.

International Search Report issued May 3, 2012 in PCT Application No. PCT/US2012/023598.

Kingma et al. "Chronic Drug Infusion Into the Scala Tympani," Journal of Neuroscience Methods, 45, 1992, pp. 127-134.

Kujawa et al. "A Nicotinic-Like Receptor Mediates Suppression of Distortion Product Otaoacoustic Emissions by Contralateral Sound," Elsevier Science B.V., Hearing Research 74, 1994, pp. 122-134.

Langer "Drugs on Target," Science, 2001, vol. 293, pp. 58-59.

Lehner et al. "A Totally Implantable Drug Delivery System for Local Therapy of the Middle and Inner Ear," ENT—Ear Nose & Throat Journal, 1997, vol. 76, No. 8, pp. 567-570.

Lintel et al. "A Piezoelectric Micropump Based on Micromachining of Silicon," Sensors and Actuators, 15, 1988, pp. 153-167.

Madou et al. "Exploitation of a Novel Artificial Muscle for Controlled Drug Delivery," Polym., Mater. Sci. Eng., vol. 83, 2000, pp. 495-497.

Mescher et al. "Surface Mount Microfluidic Flow Regulator on a Polymer Substrate," 7th International Conference on Miniaturized Chemical and Biochemical Systems, Oct. 5-9, 2003, Squaw Valley, CA, pp. 947-950.

Miller et al. "Neurotrophins Can Enhance Spiral Ganglion Cell Survival after Inner Hair Cell Loss," Int. J. Devl. Neuroscience, 199, vol. 15, No. 4/5, pp. 631-643.

Paasche et al. "Technical Report: Modification of a Cohlear Implant Electrode for Drug Delivery to the Inner Ear" Ontology & Neurology, 2003, 24, pp. 222-227.

Praetorius et al. "A Novel Microperfusion System for the Long-Term Local Supply of Drugs to the Inner Ear: Implantation and Function in the Rat Model," Audiol. Neurootol., 2001, 6, pp. 250-258.

Prieskorn et al. "Technical Report: Chronic and Acute Intraochlear Infusion in Rodents," Elsevier, Hearing Research, 140, 2000, pp. 212-215.

Santini et al. "A controlled-release microchip," Nature, vol. 397, 1999, pp. 335-338.

Schoendorf et al. "Continuous Intratympanic Infusion of Gentamicin Via a Microcatheter in Meniere's Disease," Otolaryngology—Head and Neck Surgery, vol. 124, No. 2, 2001, pp. 203207.

Shepherd et al. "A Multichannel Scala Tympani Electrode Array Incorporating a Drug Delivery System for Chronic Intracochlear Infusion," Hearing Research, 172, 2002, pp. 92-98.

Smits "Piezoelectric Micropump with Three Valves Working Peristaltically," Sensors and Actuators, A21-A23, 1990, pp. 206-206.

Sridhar et al. "Unique Postsynaptic Signaling at the Hair Cell Efferent Synapse Permits Calcium to Evoke Changes on Two Time Scales," The Journal of Neuroscience, 1997, 17(1), pp. 428-437.

US Office Action in U.S. Appl. No. 12/986,067, filed Mar. 16, 2012.

Weibel, et al. "Torque-actuated Valves for Microfluidics," Analytical Chemistry 77(15), pp. 4276-4733, Aug. 2005.

Yang, et al. "Using Compliant Membranes for Dynamic Flow Stabilization in Microfluidic Systems," Proceedings of MEMS 2005, pp. 706-709, 2005.

Yu et al. "Responsive Biomimetic Hydrogel Valve for Microfluidics," Applied Physics Letters, vol. 78, No. 17, 2001, pp. 2589-2591.

Zengerle et al. "A Bidirectional Silicon Micropump," Sensors and Actuators, A 50, 1995, pp. 81-86.

* cited by examiner

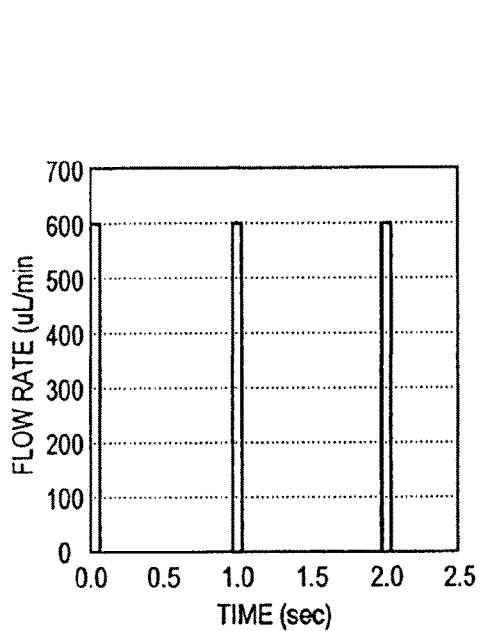
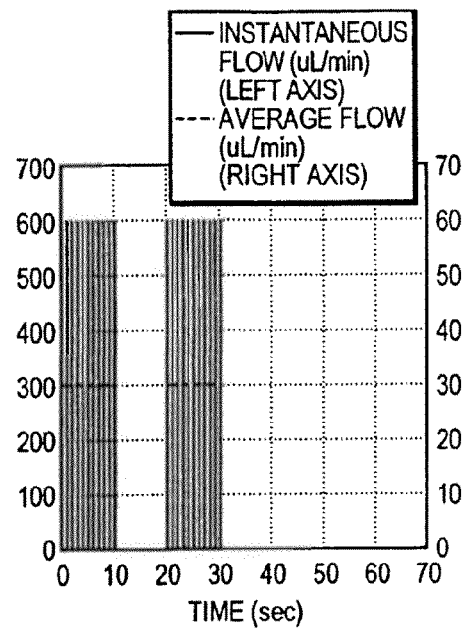
FIG. 4A
FIG. 4B
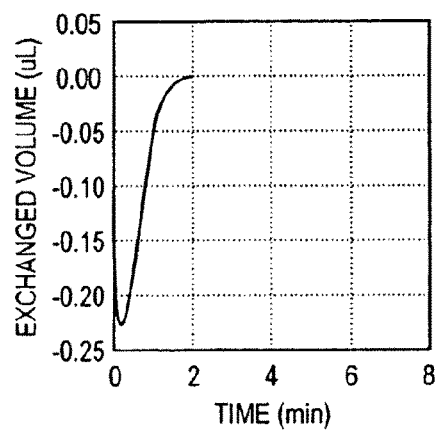
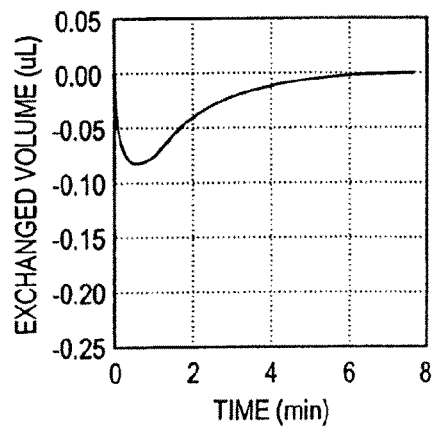
FIG. 5A
FIG. 5B

| NAME | | | DESIGN VARIATIONS | | | |
|---|---|---|---|---|---|---|
| | | | MODE 1 | | MODE 2 | |
| DESIGN DESCRIPTION | SYM-BOL | UNITS | HIGH FLOW | LOW FLOW | LOW FLOW | HIGH FLOW |
| DESIGN INPUTS | | | MODE 1 IS A CONTINUOUS MODE, NO MODULATION OF THE PUMP SIGNAL | | MODE 2 USES MODULATION OF THE PUMP SIGNAL | |
| PUMP FREQUENCY | $f_p$ | Hz | 0.014 | 0.003 | 2 | 2 |
| PUMP CYCLE TIME (1/fp) | tc | sec | 71.3 | 337.7 | 0.5 | 0.5 |
| MODULATION TIME | tm | min | | | 1.19 | 5.63 |
| STROKE VOLUME | Vstroke | uL | 0.5 | 0.5 | 0.5 | 0.5 |
| AVERAGE PUMP RATE | ISO | uL/min | 0.421 | 0.089 | 60 | 60 |
| PRIMARY FEED ID | $D_{IF}$ | mm | 1 | 2 | 1 | 2 |
| PRIMARY RETURN ID | $D_{IR}$ | mm | 1 | 2 | 1 | 2 |
| PRIMARY FEED OD | $D_{OF}$ | mm | 1.25 | 2.25 | 1.25 | 2.25 |
| PRIMARY RETURN OD | $D_{OR}$ | mm | 1.35 | 2.25 | 1.25 | 2.25 |
| PRIMARY FEED LENGTH | $L_F$ | cm | 50 | 50 | 50 | 50 |
| PRIMARY RETURN LENGTH | $L_R$ | cm | 50 | 50 | 50 | 50 |
| T FEED ID | $D_{IFT}$ | um | 75 | 75 | 75 | 75 |
| T RETURN ID | $D_{IRT}$ | um | 250 | 250 | 250 | 250 |
| T FEED LENGTH | $L_{FT}$ | mm | 50 | 10 | 50 | 10 |
| T RETURN LENGTH | $L_{RT}$ | mm | 50 | 10 | 50 | 10 |
| MIXER OUTPUT ID | $D_{IM}$ | um | 75 | 75 | 75 | 75 |
| MIXER OUTPUT LENGTH | $L_M$ | mm | 20 | 20 | 20 | 20 |

CONTINUE FROM FIG. 7A

| NAME | | | DESIGN VARIATIONS | | | |
|---|---|---|---|---|---|---|
| | | | MODE 1 | | MODE 2 | |
| DESIGN DESCRIPTION | SYM-BOL | UNITS | HIGH FLOW | LOW FLOW | LOW FLOW | HIGH FLOW |
| DESIGN INPUTS | | | MODE 1 IS A CONTINUOUS MODE, NO MODULATION OF THE PUMP SIGNAL | | MODE 2 USES MODULATION OF THE PUMP SIGNAL | |
| PRIMARY FEED RESISTANCE | $R_F$ | psi*min/uL | 3.94E-05 | 2.46E-06 | 3.94E-05 | 2.46E-06 |
| PRIMARY RETURN RESISTANCE | $R_R$ | psi*min/uL | 3.94E-05 | 2.46E-06 | 3.94E-05 | 2.46E-06 |
| T FEED RESISTANCE | $R_{FT}$ | psi*min/uL | 1.25E-01 | 2.49E-02 | 1.25E-01 | 2.49E-02 |
| T RETURN RESISTANCE | $R_{RT}$ | psi*min/uL | 1.01E-03 | 2.02E-04 | 1.01E-03 | 2.02E-04 |
| OUTPUT RESISTANCE | $R_M$ | psi*min/uL | 4.98E-02 | 4.98E-02 | 4.98E-02 | 4.98E-02 |
| FEED BUBBLE LENGTH | $L_{FB}$ | mm | 0.0 | 0.0 | 0.0 | 0.0 |
| FEED INITIAL BUBBLE PRESSURE | $P_{FBO}$ | psi*min/uL | 14.0 | 14.0 | 14.0 | 14.0 |
| AVERAGE OPER. BUBBLE PRESSURE (FEED) | $P_{FBA}$ | psi*min/uL | 14.0 | 14.0 | 14.0 | 14.0 |
| FEED BUBBLE CAPACITANCE | $C_{FB}$ | uL/psi | 0.0 | 0.0 | 0.0 | 0.0 |
| FEED TUBE COMPLIANCE CAPACITANCE | $C_{FC}$ | uL/psi | 2.1 | 16.5 | 2.1 | 16.5 |
| PRIMARY FEED CAPACITANCE | $C_F$ | uL/psi | 2.1 | 16.5 | 2.1 | 16.5 |
| RETURN BUBBLE LENGTH | $L_{RB}$ | mm | 0.0 | 0.0 | 0.0 | 0.0 |
| RETURN INITIAL BUBBLE PRESSURE | $P_{RBO}$ | psi | 14.0 | 14.0 | 14.0 | 14.0 |
| AVERAGE OPER. BUBBLE PRESSURE (RETURN) | $P_{RBA}$ | psi | 14.0 | 14.0 | 14.0 | 14.0 |
| RETURN BUBBLE CAPACITANCE | $C_{RB}$ | uL/psi | 0.0 | 0.0 | 0.0 | 0.0 |
| RETURN TUBE COMPLIANCE | $C_{RC}$ | uL/psi | 2.1 | 16.5 | 2.1 | 16.5 |
| PRIMARY RETURN CAPACITANCE | $C_R$ | uL/psi | 2.1 | 16.5 | 2.1 | 16.5 |
| MAXIMUM PUMP P | $P_{max}$ | psi | | | 7.5 | 1.5 |
| CYCLE VOLUME | $V_{cyc}$ | uL | -0.223 | -0.085 | -15.29 | -24.46 |
| MAXIMUM FLOW RATE | $f_{max}$ | uL/min | -0.390 | -0.040 | -26.75 | -10.15 |

FIG. 7B

DRUG DELIVERY APPARATUS

CROSS-REFERENCE TO RELATED APPLICATION

This application claims priority to and the benefit of U.S. Provisional Patent Application No. 61/438,934, filed Feb. 2, 2011, which is incorporated herein by reference in its entirety.

STATEMENT REGARDING FEDERALLY SPONSORED RESEARCH OR DEVELOPMENT

This invention was made with government support under Grant No. 2 R01 DC006848-04A1 awarded by the National Institutes of Health. The government has certain rights in the invention.

FIELD OF THE INVENTION

The present invention relates generally to the field of drug delivery devices employing catheters and/or cannulas to transport fluid from a reservoir to a patient and, more particularly, to a device for introducing a drug into a patient's bodily fluid, such as, for example, into perilymph in the human ear, as well as to methods for infusing drugs into cochlea for treatment of hearing loss and other disorders of hearing and vestibular function.

BACKGROUND OF THE INVENTION

Sensorineural hearing loss (SNHL) is common, and its impact on human communication and quality of life is significant. It is estimated that some 28 million individuals in the United States suffer from hearing loss. As our population ages, hearing loss prevalence is expected to climb rapidly, nearly doubling by the year 2030. Causes range from degenerative processes associated with aging and genetic disorders to environmental exposure to loud sounds and toxic agents. Consequences range from moderate communication difficulty and social withdrawal to profound deafness and its significant challenges. At present, management of SNHL centers on the use of hearing aids and cochlear implants. However, such treatments cannot address hearing loss prevention, cannot minimize hearing loss progression and, even with optimal device fitting, cannot increase a damaged ear's basic capacity. As a result, many users continue to experience significant communication difficulties.

Recent advances in the pharmacology and molecular biology of hearing have revealed new and powerful possibilities for preventing or minimizing hearing loss. The crux of the problem in SNHL is loss of the delicate cochlear sensory cells that detect the exquisitely small mechanical vibrations associated with sound. In human ears, once lost or damaged, these sensory cells do not regenerate and this compromise is often followed by secondary degeneration of auditory neurons. However, scientists and clinicians are making rapid progress in understanding the molecular mechanisms associated with cochlear and auditory nerve degenerative processes. Additional insight into the molecular signals involved in generating new hair cells is rapidly accumulating, and with this insight comes the promise of novel and precise drug treatments. Moreover, the extraordinary progress that has been made in defining the genes involved in a number of human genetic forms of deafness offers hope for gene-transfer and molecular approaches to treat these diseases.

For therapies based on these discoveries to become clinically useful, it will be necessary to develop safe and reliable mechanisms for the delivery of complex compounds into the inner ear. Direct delivery to the fluids of the inner ear is necessary because of the presence of a blood-labyrinth drug barrier, which is anatomically and functionally similar to the blood-brain barrier. That is, through the presence of so-called 'tight junctions' between adjacent cells in the inner ear end organs, substances outside these organs encounter a substantial physical barrier to entry, thus protecting the delicate sensory structures within from insult. This 'protection', however, also prevents certain molecules with potentially therapeutic effect from gaining access to their inner ear targets. Prime candidates for exclusion from the cochlea after systemic injection are complex molecules, such as proteins and peptides, as well as any molecule that is not lipid-soluble.

Current otologic practice requires drug delivery to the inner ear, but uses inefficient routes. Drugs are commonly delivered systemically, with the hope that they will find their way to their intended inner ear targets in the form and concentration desired and without serious side effects. Systemic corticosteroids, for example, are used in the otologic management of idiopathic sudden and immune-mediated SNHL. Their clinical usefulness, however, is limited by undesirable side effects arising from the high systemic doses required to achieve sufficient cochlear fluid levels of drug to produce the intended inner ear effects.

Local drug application by transtympanic perfusion of the middle ear with the goal of diffusion through the round window membrane (RWM) into the fluid spaces on the inner ear was introduced nearly 50 years ago with aminoglycoside treatment of Meniere's disease. This method or some variant remains in common use in the treatment of inner ear diseases, notably the intractable vertigo that can be associated with Meniere's disease, but has been used as well for sudden SNHL, autoimmune inner ear disease, and even tinnitus. Accomplished as an office procedure, a drug is injected through the tympanic membrane into the middle ear space. The patient then lies with the treated ear 'up' so that the drug has a better chance of making contact with the RWM, through which the drug must diffuse to gain access to the inner ear. With the goal of extending the time of drug availability to the inner ear, newer methods of intratympanic drug delivery have employed several strategies to prolong drug contact with the RWM, including placing absorbent material on or near the RWM and using pump-driven microcatheter systems.

Delivery of drugs to the middle ear reduces systemic side effects, but access to the inner ear is unpredictable. Middle ear application has advantages over systemic drug delivery, in that drugs so applied can reach their desired targets at higher concentrations and without unwanted systemic side effects. The application is straightforward, and complications are minimal. A major limitation of these methods, however, is the inability to precisely control the amount of drug that diffuses from the middle ear through the RWM into the inner ear. Individual variation in mucous membrane thickness, mucosal folds and middle ear anatomy can have a significant impact on the amount of drug that ultimately enters the inner ear. Some commentators, for example, report round window niche obstruction in 33% of human ears. This becomes even more problematic when considering delivery of coplex macromolecules with limited diffusion coefficients and those requiring sequenced delivery. Additionally, the bolus application used by certain existing systems makes them poorly suited for direct inner ear delivery. Although such devices may be useful for delivery of low molecular weight, stable, lipid-soluble compounds like steroids, they would not be suitable for the delivery of the unstable macromolecules that ultimately will be the therapeutic compounds with greatest potential benefit.

Direct intracochlear drug delivery, which has been utilized successfully in animals, has significant potential advantages for therapeutic application. The practice of placing drugs of interest within cochlear perilymphatic spaces via a perfusion technique is a method with a long history of successful application. When carefully administered, the technique itself has been shown to have little effect on a variety of gross cochlear and neural potentials as recorded from sites within and near the cochlea. This mode of delivery bypasses the blood-cochlea barrier, allowing drugs to reach their intended targets more directly with lower doses and fewer non-specific actions. Drugs are largely unaltered by metabolic changes that inevitably occur with other routes of administration. Drugs perfused into the perilymph compartment of scala tympani have ready access to the hair cells and synaptic regions of hair cells, a view supported by investigations in which various stains demonstrated ready access to structures within the organ of Corti when introduced via the scala tympani perilymph compartment. Additionally, a comparison of the concentrations of cholinergic antagonists required to block the cochlear efferents in vivo and those effective at in vitro isolated outer hair cells shows remarkably close agreement.

Thus, in order to treat ear disorders, it may often be necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Finn discloses a hollow, cylindrical tube manufactured of sponge material, e.g. dehydrated cellulose, which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes.

However, as mentioned above, the delivery of therapeutic agents in a controlled and effective manner is considerably more difficult with respect to tissue structures of the inner ear (e.g. those portions of the ear surrounded by the otic capsule bone and contained within the temporal bone, which is the most dense bone tissue in the entire human body). The same situation exists in connection with tissue materials, which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) that include these components. Access to these and other inner ear tissue regions is typically achieved through a variety of structures, including but not limited to the round window membrane, the oval window/stapes footplate, the annular ligament, and the otic capsule/temporal bone, all of which shall be considered "middle-inner ear interface tissue structures" as described in greater detail below. Furthermore, as indicated herein, the middle ear shall be defined as the physiological air-containing tissue zone behind the tympanic membrane (e.g. the ear drum) and ahead of the inner ear.

The inner ear tissues listed above are of minimal size and only readily accessible through invasive microsurgical procedures. In order to treat various diseases and conditions associated with inner ear tissues, the delivery of drugs to such structures is often of primary importance. Representative drugs that are typically used to treat inner ear tissues include but are not limited to urea, mannitol, sorbitol, glycerol, lidocaine, xylocalne, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. The treatment of inner ear tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hydrops, endolymphatic hypertension, perilymphatic hypertension, perilymphatic hydrops, perilymphatic fistula, intracochlear fistula, Meniere's disease, tinnitus, vertigo, hearing loss related to hair cell or ganglion cell damage/malfunction, and ruptures in various membrane structures within the ear.

With respect to existing methods of drug delivery, implantable and externally mounted drug infusers use a "one-way" infusion system where a reservoir empties into the tissue directly or through a catheter. To be pumped along a catheter, however, drugs must have appropriate physical properties. For example, it has been determined that dry compounds, which may be more stable than aqueous ones, cannot be used in a conventional infuser. In another example, it has been determined that highly concentrated compounds may be prohibited because of local reaction at the catheter outlet. Moreover, in the application to inner ear diseases, dosage to the relevant tissues of the cochlea can be difficult or impossible to assess and control by the methods described above, and no device has been provided for programmable long-term delivery, either to the middle ear or inner ear.

Known methods require a relatively complicated mechanism to achieve mixing and circulating flow between reservoir and patient. These more complicated methods include having two tubes entering the patient, rather than just one, or having a two-way pump, two pumps, or a switching valve at the pump.

For example, drugs are delivered to the inner ear by infusing the middle ear and allowing the medication to diffuse through the local tissue and into the inner ear. Alternatively, drugs are given systemically (e.g., orally or by injection). For example, U.S. Pat. No. 5,895,372 to Zenner, incorporated by reference herein, discloses an implantable dosaging system that injects drugs into the middle ear using a manually operated pump. As another example, U.S. Pat. No. 6,685,697 to Arenberg et al., incorporated by reference herein, describes a drug delivery unit for controlled delivery of a therapeutic agent to an internal cavity of the ear, particularly to the inner ear, that includes carrier media material containing one or more therapeutic agents therein. The carrier media material is designed to release the therapeutic agents in a controlled manner over time. The drug delivery unit is shaped and sized for placement of at least a portion thereof in the round window niche of a patient.

It may be advantageous to use reciprocating flow, meaning that a volume of fluid is alternately injected into and then withdrawn from the organ. In such cases, the reciprocating flow may be driven by a device that is connected to the organ by a cannula. The device is typically pre-loaded with a carrier fluid, which is the endogenous fluid of the organ or a similar solution. Over time, because of diffusion and mixing, the endogenous fluid and the fluid inside the device are essentially the same.

The reciprocating flow provides a mechanism for transporting drug from the device to the organ. The drug may itself be in solution or in another form, such as a soluble solid. Moreover, the drug may be stored in such a way that it can be gradually released into the reciprocating carrier fluid. In general, the carrier fluid transports at least a portion of the released drug into the organ, where it then reaches the desired tissues by diffusion and mixing. The drug release may be repeated or may occur at a slow rate relative to the reciprocating cycle, such that the drug is delivered to the organ over an extended period, for example over months or years.

Alternatively, body fluid is caused to circulate through a drug-containing reservoir via a recirculating system having two tubes—one for inflow and one for outflow between reservoir and patient. For example, U.S. Pat. No. 5,643,207 to Rise, incorporated by reference herein, describes recirculating body fluid through a drug delivery device for drug delivery to the brain. As another example, U.S. Pat. No. 6,561,997 to Weitzel et al. discloses a circuit for extracorporeal treatment of a body fluid.

As another example, one known perfusion technology involves a cochlear implant electrode modified to allow intracochlear drug delivery. In conventional use, the electrode is inserted into the cochlea and used to provide stimulation to the auditory nerve of severely to profoundly hearing impaired individuals. The electrode employed for the drug delivery application, however, contains a removable stylet used for positioning the electrode during insertion. With the stylet removed, the lumen that remains provides the path for drug delivery. The lumen is connected to an osmotic or mechanical pump via a connector and short length of perfusion tubing.

Notably, existing drug-delivery technology is typically not appropriate for long-term programmable infusion into the inner ear. The existing approaches for drug delivery devices include external and implanted infusers, osmotic pumps, and erodible polymer-drug systems. These systems range from passive devices, which have a low level of predictability in their dispense rates, to electronically-controlled rate dispensers, and finally to fully programmable infusers. Device volumes range from pill size (e.g., those available from Oculex Pharmaceuticals) to over ten cubic inches, generally depending on their maximum dispense volume and sophistication of control. Though small in volume, erodible polymer and porous membrane systems (e.g., those available from iMMED, Inc.) must typically be implemented to deliver a specific compound or, at best, a set of compounds with similar chemistry and transport properties. They are generally short to medium term delivery devices (less than six weeks) with unalterable, non-constant delivery profiles. The existing osmotic pump-based delivery systems (e.g. those available from Alzet International) are similar in terms of device size and lifetime, and they too are capable only of fixed rate delivery. The various available models trade off device size, lifetime, and delivery rate, depending on the application requirements. Infuser technology has primarily been developed by Medtronic (Minneapolis, Minn.). Devices such as the SynchroMed product offer sophisticated control and are effective for treatment for some disorders such as chronic pain. However, because they use macro scale conventionally fabricated pumps, these systems are relatively large. They are practical only when implanted in subcutaneous tissue in the torso.

Emerging microsystems present solutions to many previously intractable bioengineering challenges. The extension of micorfabrication methods from integrated circuits to many other applications has spawned microelectromechanical systems (MEMS) devices capable of reproducing the functions of conventional sensors and actuators at a fraction of the size and cost. The resulting miniaturization enables complete systems to be integrated into devices small enough to be implanted in close proximity to the organ to be treated. In the case of drug delivery, complex automated dosing regimens can be programmed into the system or even implemented to respond to sensor input of physiological measurements. Several technologies have emerged that may allow controlled release of drug in dried or lyophilized form from discrete compartments.

In one particular example, the device includes a 'working chamber' that is mechanically compressed to dispense a volume of carrier fluid through a cannula. When the chamber is restored to its initial state, fluid is withdrawn into the cannula. A flow of drug solution may be superimposed on the reciprocating flow at an independent rate, introduced to the working chamber where the drug mixes with the carrier fluid, and periodically transferred to the patient's organ by the reciprocating flow. The devices may use pump or pump-like components to produce a reciprocating, pulsatile, fluid output with controllable pulse volume and flow rate. This exemplary method may be effective for some applications, but is generally not effective when clinical requirements necessitate specific flow conditions, when a particular form of drug storage is desired, or when power conservation is a major factor in system design.

And so, as described above, developments in cochlear physiology and molecular biology allow for new and innovative ways of treating and preventing SNHL. It is desirable to implement a safe and reliable mechanism for delivering bioactive compounds directly to the inner ear, e.g., a versatile long-term drug delivery system for the treatment of inner ear disorders that will have broad application and the potential for revolutionizing the treatment of hearing loss.

Thus, it is desirable to provide an implantable long-term drug delivery system for the treatment of inner ear disorders and the prevention of SNHL, specifically, a versatile device that is capable of delivering multiple simple and complex molecules over long periods of time, with capability to control and regulate the sequence and rate of delivery, particularly through recirculating flows. Such a device can be useful for treatment of idiopathic and inflammatory conditions affecting the inner ear, including autoimmune inner ear disease, cisplatinum-induced ototoxicity, and possible Meniere's disease. In addition, a wide spectrum of other degenerative inner ear disorders may be amenable to treatment with such a device, including idiopathic, genetically-based, and age-related progressive SNHL.

SUMMARY OF THE INVENTION

In general, in one aspect, embodiments of the invention feature a drug delivery apparatus for delivering a drug into a bodily fluid in a bodily cavity over a period of time. The apparatus includes a delivery channel, having an outlet, for facilitating fluid flow through a lumen thereof to and from the bodily cavity, means for loading drug into the delivery channel while producing substantially negligible flow at the outlet, and a first actuator for driving the drug and carrier fluid through the delivery channel, out the outlet, and into the bodily cavity.

In various embodiments of the invention, the means for loading drug into the delivery channel while producing substantially negligible flow at the outlet includes a drug supply reservoir for holding the drug and a waste reservoir for receiving the carrier fluid. The drug supply reservoir may be fluidically coupled with the delivery channel via a drug supply valve, while the waste reservoir may be fluidically coupled with the delivery channel via a waste valve. The means for loading drug into the delivery channel while producing substantially negligible flow at the outlet may also include a control system for controlling the drug supply valve, the waste valve, and the first actuator so as to deliver the drug to the bodily cavity with a controlled degree of dilution (e.g., in a substantially undiluted form). Further, the means for loading drug into the delivery channel while producing substantially negligible flow at the outlet may also include a second actuator for delivering the drug into the delivery channel. The second actuator may cause drug to flow into the delivery channel at a substantially similar rate to the rate at which the first actuator causes the drug and carrier fluid to flow along the delivery channel.

In some embodiments, the drug supply reservoir is a pressurized reservoir. The apparatus may also include a sensor for measuring properties of an endogenous fluid that enters the apparatus. In certain embodiments, the apparatus is adapted to be integrated with a cochlear prosthesis, such as a device for electrically stimulating an auditory system. The apparatus may be adapted to deliver drugs to the cochlea to treat hearing disorders, to reduce side effects of implant surgery, and/or to improve performance of the prosthesis.

In other embodiments, the means for loading drug into the delivery channel while producing substantially negligible flow at the outlet includes (i) a reservoir in fluid communication with the delivery channel, and (ii) a dosing pump for driving the drug from the reservoir into the delivery channel and for pulling at least a portion of the carrier fluid out from the delivery channel and into the reservoir.

In various embodiments, the reservoir features a reservoir channel of greater length than a length of the delivery channel. The reservoir channel length may be greater than both a width and a height of the reservoir channel. The reservoir may be formed in a flat sheet of polyimide. In some embodiments, the dosing pump is configured to drive drug in only one direction, and/or to deliver at least 200 nL per stroke.

In general, in another aspect, embodiments of the invention feature a method for delivering a drug into a bodily fluid in a bodily cavity over a period of time. The method includes loading drug from a drug supply reservoir into a delivery channel while producing substantially negligible flow at an outlet of the delivery channel, and subsequently activating an actuator to drive the drug and carrier fluid through the delivery channel, out the outlet, and into the bodily cavity.

In one embodiment, loading the drug from the drug supply reservoir into the delivery channel while producing substantially negligible flow at the outlet of the delivery channel includes opening a drug supply valve to allow the drug from the drug supply reservoir to enter the delivery channel, opening a waste valve to allow at least a portion of the carrier fluid in the delivery channel to enter a waste reservoir, closing the drug supply valve after a desired amount of the drug has entered the delivery channel, and closing the waste valve prior to the drug entering the waste reservoir. In various embodiments, a volume of the drug entering the delivery channel displaces an equal volume of the carrier fluid present in the delivery channel into the waste reservoir, such that flow is not generated at the outlet. The method may also include reversing the actuator to reverse carrier fluid flow after delivery of the drug through the outlet.

In another embodiment, loading the drug from the drug supply reservoir into the delivery channel while producing substantially negligible flow at the outlet of the delivery channel includes activating a dosing pump to drive the drug from the drug supply reservoir into the delivery channel and to pull at least a portion of the carrier fluid out from the delivery channel and into the drug supply reservoir, and deactivating the dosing pump after delivering a predetermined amount of the drug into the delivery channel. A volume of drug driven into the delivery channel may be substantially equal to a volume of the carrier fluid pulled into the drug supply reservoir.

In various embodiments, the drug supply reservoir features a reservoir channel of greater length than a length of the delivery channel. The reservoir channel length may be greater than both a width and a height of the reservoir channel. In some embodiments, the drug supply reservoir is formed in a flat sheet of polyimide. The dosing pump may drive drug in only one direction, and may deliver at least 200 nL per stroke. The dosing pump may be deactivated after a single stroke. In various embodiments, the pump actuator includes a reciprocating membrane. The actuator may, for example, be activated so as to deliver a pulsed flow, thereby preventing or reversing occlusion of the delivery channel.

In general, in yet another aspect, embodiments of the invention feature a drug delivery apparatus for delivering a drug into a bodily fluid in a bodily cavity over a period of time. The apparatus includes a cannula for facilitating fluid flow through a lumen thereof to and from the bodily cavity, and at least one hollow member defining a lumen in fluid communication with the cannula. The at least one hollow member and the cannula are adapted to fill with fluid at a different rate than the rate at which fluid empties from the at least one hollow member and the cannula. The apparatus also includes a check valve, having a leak path, that is located within the cannula or the at least one hollow member, and an actuator (adapted to operate non-continuously) for driving fluid through the at least one hollow member and the cannula.

In various embodiments of the invention, the actuator includes a linear motor, a rotating motor with a cam, a solenoid with a latching mechanism, an electromagnet with a latching mechanism, a solenoid with bistable modes, or an electromagnet with bistable modes.

The apparatus may also include a drug storage element in fluid communication with the at least one hollow member. The drug storage element may have multiple compartments, each of which is separated from the at least one hollow member by a single-use valve. In various embodiments, the drug storage element has an erodible solid or a polymer configuration so that drug is continuously and passively released into the fluid. The apparatus may be adapted to release multiple compounds, each at separate time intervals, so as to perform treatment according to a chosen therapeutic sequence.

In some embodiments, the apparatus includes a sensor for measuring properties of an endogenous fluid that enters the apparatus. The apparatus may be adapted to be integrated with a cochlear prosthesis for electrically stimulating an auditory system, to deliver drugs to the cochlea to treat hearing disorders, to reduce side effects of implant surgery, and/or to improve performance of the prosthesis.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 4A is a plot of an example pump flow output for a pump operating at a constant frequency, in accordance with one embodiment of the invention.

FIG. 4B is a plot of an example flow rate for a pump which is periodically turned on and off at a frequency lower than the pump cycle frequency, in accordance with one embodiment of the invention.

FIG. 5A is a plot of an example output flow for one example delivery system design with a pump operating at a constant frequency, in accordance with one embodiment of the invention.

FIG. 5B is a plot of a second example output flow for one example delivery system design with a pump operating at a constant frequency, in accordance with one embodiment of the invention.

FIGS. 7A-7B are together a table of performance data for exemplary embodiments of the invention.

DETAILED DESCRIPTION

Figure 1:
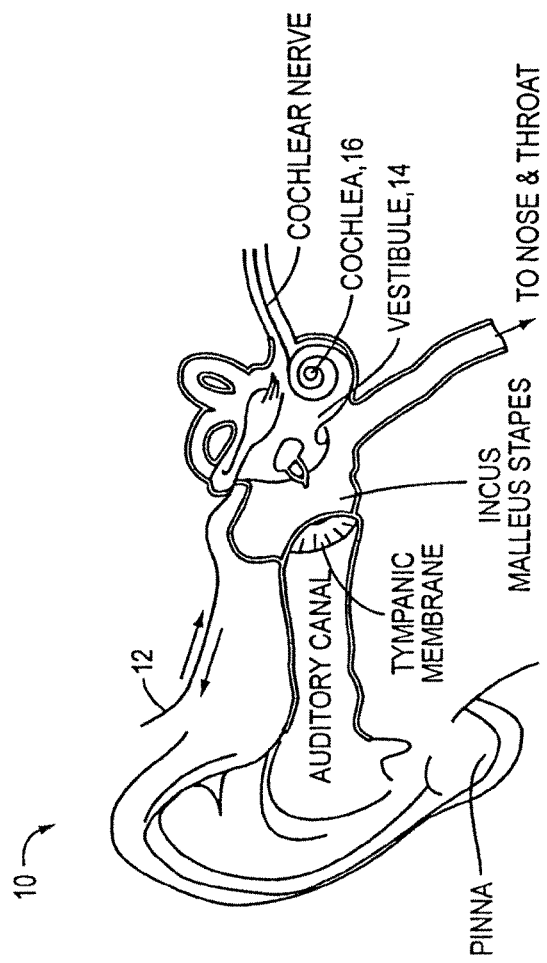
FIG. 1 depicts a sketch of a human inner ear with an implanted drug delivery system, in accordance with various embodiments of the invention.

As discussed above, conventional drug infusers utilize macroscale machined components to pump liquid drugs from a reservoir. Various embodiments of the present invention replace these components with a synthesis of micropumps and MEMS solutions for drug storage and release, which results in smaller devices with greater functionality. This opens up the inner ear and other previously inaccessible locations in the body to new direct treatment, without the side effects of systemic delivery.

Microfluidics and microelectromechanical systems (MEMS) capability can be used for drug delivery applications, to allow or provide a controlled rate, low drug volume, and/or liquid formulation (e.g., for an implantable inner ear delivery system). In an example embodiment, a fluidic system having a closed loop microfluidic flow controller can be used with animal test apparatus. In one embodiment of the current invention, an implanted recirculating delivery system can be used in therapy for hearing loss and Meniere's disease. An example delivery system may employ a number of commercially available pumps, such as, but not limited to, a Wilson Greatbatch insulin pump or MEMS pump, such as those available from Debiotech (Lausanne, Switzerland).

In some embodiments, the micromechanical device for intracochlear drug delivery utilizes a surgical approach that is similar to cochlear implantation, but minimizes cochlear insult. The implementation concept includes a double lumen intracochlear catheter inserted into scala tympani through a cochleostomy adjacent to the round window. In its implanted position, it is similar to cochlear implants that also traverse the tympanomastoid cavity with electrodes positioned within the cochlea, except that the depth of insertion is much less.

In accordance with embodiments of the invention, drug delivery to the ear relies on a method in which a recirculating stream of fluid from the patient is passed through a device and is infused remotely rather than within the tissue, which enables recirculation and control of very low flow rates (e.g., less than 1 microliter/minute) as required in the confined volume of the inner ear. A specific application with respect to inner ear diseases provides for direct infusion of the cochlea through a catheter, using an implanted device to programmably and continually deliver drugs through the catheter.

The recirculating fluid permits the drug reservoir to contain a highly concentrated solution, and therefore can potentially produce a device that operates for years without refilling. This greatly reduces the risk of microbial contamination during refill. Another benefit is using a vehicle that is inherently biochemically compatible. In addition, the perilymph may circulate through the catheter at a rate that is independent of the drug delivery rate. Thus, these parameters can be optimized separately. It is likely that frequent circulation of the perilymph will maintain patency in the catheter, whereas a slow one-way drug infusion would occlude. Finally, because there is controlled supply of liquid solvent, it is not necessary to use a liquid drug reservoir. The drug storage could take any number of forms, such as microchip arrays, bio-erodible polymers, or even hybrid combinations of these drug delivery methods.

In a specific exemplary embodiment, a microfluidic pump recirculates human perilymph, which is withdrawn and returned to the inner ear through a catheter, implanted through the round window membrane or adjacent tissue. Drugs are injected into this recirculating stream from one or more reservoirs by one or more microvalves and/or one or more other drug release methods.

As used herein, the term "drug" is understood to mean any natural or synthetic, organic or inorganic, physiologically or pharmacologically active substance capable of producing a localized or systemic prophylactic and/or therapeutic effect when administered to an animal. A drug includes (i) any active drug, (ii) any drug precursor or pro-drug that may be metabolized within the animal to produce an active drug, (iii) combinations of drugs, (iv) combinations of drug precursors, (v) combinations of a drug with a drug precursor, and (vi) any of the foregoing in combination with a pharmaceutically acceptable carrier, excipient, or formulating agent.

The drug or drugs of interest may be stored in the apparatus either in pure form or as a formulation, for example in combination with a pharmaceutically acceptable carrier or encapsulated within a release system. The release system can include a matrix of a biodegradable material or a material which releases incorporated drug by diffusion. The drugs can be homogeneously or heterogeneously distributed within the release system. A variety of release systems may be useful in the practice of the invention, however, the choice of the appropriate system will depend upon the rate of drug release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar. Release systems may be natural or synthetic. However, synthetic release systems are preferred because generally they are more reliable, are more reproducible, and produce more defined release profiles. The release system material can be selected so that drugs having different molecular weights are released from a particular cavity by diffusion through or degradation of the material. Biodegradable polymers, bio-erodible hydrogels, and protein delivery systems currently are preferred for drug release via diffusion or degradation.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Preferably, the storage capabilities of the apparatus are such that it holds a sufficient amount of the drug to provide a continuous delivery over the extended delivery period, e.g., several weeks, months, or even longer. The storage volume needed thus depends on characteristics such as drug solubility, drug delivery rate, period of delivery, drug's half life, etc. Once implanted, the device continuously delivers the drug for a prolonged period of time until replenishment. In other embodiments, the device delivers the drug in a non-continuous fashion (e.g., intermittently over time).

In various embodiments of the invention, communication with a remote device external to the patient's body and capable of controlling the infusion rate allows for modification of the therapy in response to a patient's symptoms and reactions. This feature may include control of the recirculation rate to allow different dosage schemes, such as, but not limited to, either steady low concentrations or intermittent high concentrations of drugs. Variation of the dosage based on the time of day can also be desirable.

In addition to performance features, a number of safety features may also be included in embodiments of the invention. Example features may include, but are not limited to, automatic shutoff control if pressure or flow sensors give abnormal readings, self-diagnostic routines which may run automatically or upon prompting from an external controller. In one embodiment of the invention, telemetry can enable a physician to interrogate settings, identify low battery or other alarm signals, and obtain device identification or serial number. A clinician may communicate with the device by means of a hand-held module connected to a personal computer, or through another analogous communication device.

The ability to communicate with implanted electronic devices has been well established over the last 25 years (e.g. with pacemaker systems). As such, communicating with and controlling the drug delivery device does not pose a major problem. Nonetheless, the communication subsystem must guarantee reliable and robust operation, since minimal service and adjustment is possible after installation.

As a result of its ubiquitous application, communication via the wireless RF technique offers one approach for remote communication. In addition to enabling a small low-cost device, the RF technique also provides a convenient means by which the battery energy may be replenished. Although recent studies have concentrated on frequencies above a few hundred megahertz, these studies have been motivated by the need to distribute real-time image information. The bandwidth requirements for the drug delivery device are much more modest. A frequency of 10 MHz helps minimize attenuation due to skin effect, while at the same time allows use of a small, low profile antenna.

Several additional physical means are also available for coupling communication signals from the implanted device to an external interrogator or programmer. In one embodiment of the invention, mechanical (acoustic) waves may provide a communication mechanism. The acoustic technique is enabled by the recent availability of miniature transducers fabricated with MEMS technology. Further embodiments may include, but not be limited to, the use of optical means or direct volume conduction to communicate with an implanted device.

Referring to FIG. 1, in one embodiment, an implanted recirculating delivery system directs fluid to and from the cochlea of a human ear 10. A double lumen catheter 12 is implanted in a body and is in communication with the vestibule 14 and cochlea 16 of the inner ear. This arrangement allows a fluid to recirculate between the cochlea 16 and an external or internally implanted pump (not shown).

Figure 2B:
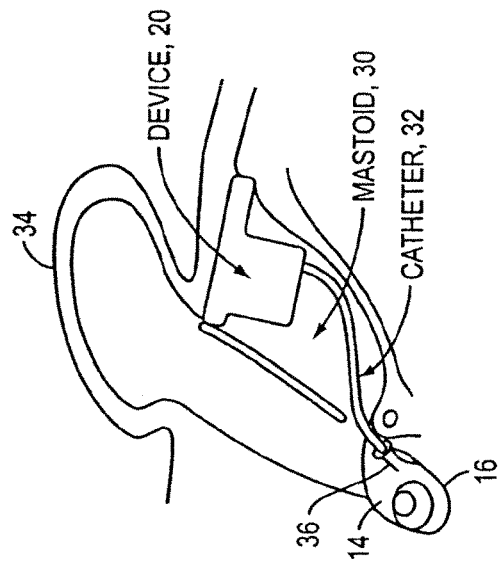
FIG. 2B depicts a sketch of a exemplary drug delivery apparatus implanted in the mastoid cavity of a human ear.
Figure 2A:
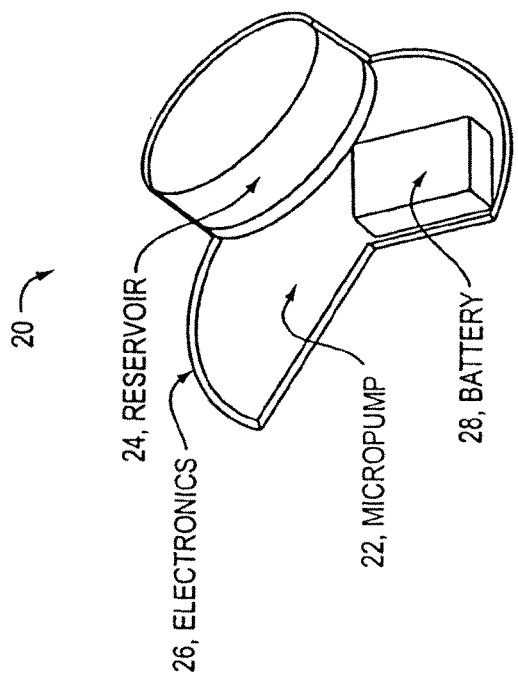
FIG. 2A is a schematic view of an exemplary drug delivery apparatus that includes a pump, a reservoir, electronics, and a battery system, in accordance with one embodiment of the invention.

An exemplary embodiment of the invention with an electronic device imbedded within the mastoid cavity of a human ear can be seen in FIGS. 2A-2B. In FIG. 2A, a device 20 includes a micropump 22 connected to a reservoir 24. The flow rate produced by the pump 22, and the rate at which a drug is released by the reservoir 24, can be controlled by control system 26 integrated within the device 20. Power can be supplied to the system through a battery 28, which can also be imbedded in the device 20. Alternative embodiments of the device 20 may incorporate additional features, such as but not limited to further reservoirs or additional electronic features, but can also be simplified by removing attachments shown herein, such as the reservoir 24. For example, drug storage within the device can be achieved through a number of methods such as, but not limited to, the use of a fluid chamber with a valve connection, the addition of bio-erodible polymers, the addition of multiple reservoirs 24 containing multiple drugs, and the addition of storage devices capable of delivering solid or powdered drug formulations.

The device 20 shown in FIG. 2A can be seen implanted within the mastoid cavity 30 of a human ear, in accordance with one embodiment of the invention. In the embodiment depicted in FIG. 2B, the device 20, incorporating the micropump 22, reservoir 24, control system 26, and battery 28, is implanted behind the pinna 34 of a human ear, within the mastoid cavity 30. The device is connected to a double-lumen catheter 32, which connects to an interface member, in this case a cannula 36, which is implanted into the vestibule 14 of a human ear, thus allowing fluid communication with a cochlea 16.

Various configurations of the device allow a drug, or drugs, to be mixed with the therapeutic fluid recirculating within the double-lumen catheter 32. Depending upon the requirements of the system, the infusion of a drug into the therapeutic fluid can be constant or modulated. The flow rate of the therapeutic fluid within the system can also be controlled through the control of the micropump 22, which can either be held at a substantially constant frequency or modulated. The control system 26 in the device can control the flow and infusion rate, and also provides the possibility of monitoring the performance of the device 20, sending information regarding the flow parameters to a remote device, and receiving information from a remote device. In various embodiments, the device includes a regulating system that is used to determine optimal drug delivery rates. In some embodiments, the regulating system is part of the control system 26. In one particular embodiment, a biosensor of the regulating system detects a level of a particular molecule of the drug and thereby enables the regulating system to automatically determine the quantity of the drug to release from the reservoir. Also, a sensor of the regulating system could also measure the concentration of drug in the perilymph and provide feedback to regulate the drug release rate from the reservoir or increase the flow rate by the pump.

Figure 3A:
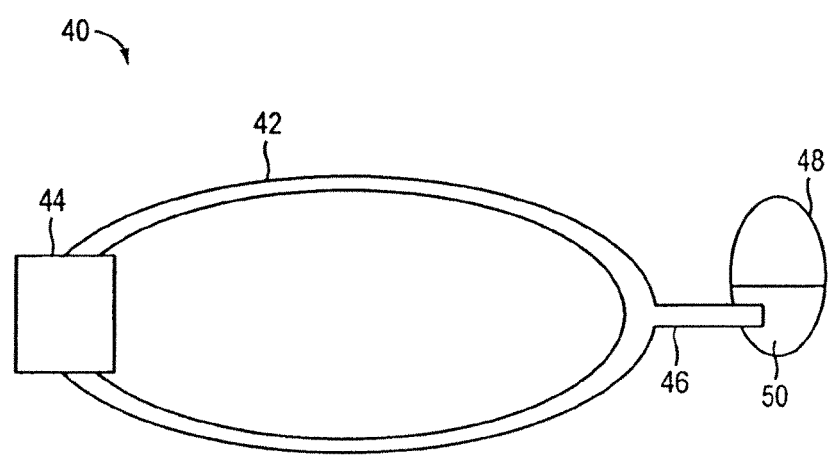
FIG. 3A is a schematic view of a recirculating drug delivery apparatus in accordance with some embodiments of the invention.
Figure 3B:
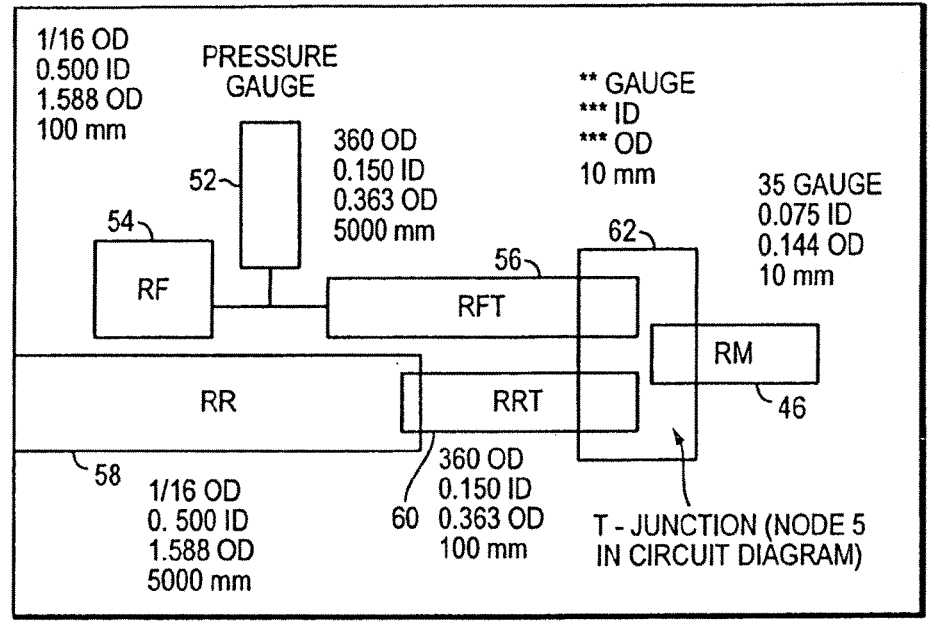
FIG. 3B-3C depict schematic diagrams for the drug delivery apparatus of FIG. 1A.
Figure 3C:
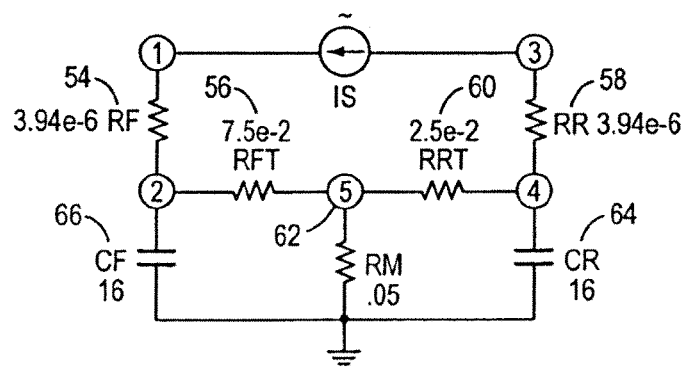

A schematic for the basic fluid circuit is shown in FIGS. 3A to 3C. Referring to FIG. 3A, in one embodiment, a drug delivery system 40 has been designed without a distinct supply reservoir. As a result, it recirculates a constant net volume of fluid through a substantially closed loop of tubing 42 driven by a micropump 44. The recirculating stream communicates through a lumen of a cannula 46 with the cochlea 48, depicted here for simplicity as an open reservoir containing fluid 50. Delivery occurs through transport outside of the system: fluid expelled or discharged during the first half pump cycle equilibrates with the fluid in the outside reservoir, either through diffusion or mixing, thus the fluid drawn in during the next half cycle is less concentrated and net delivery occurs, albeit decreasing over time. In various embodiments, design of the system 40 enhances mixing by achieving an oscillatory flow of sufficient amplitude to completely expel the fluid contained in the cannula 46 during a cycle. Otherwise, "fresh" compound would not be delivered each cycle; in effect, mixing would largely be dominated by diffusion in the small volume of the cannula 46.

FIGS. 3B and 3C, respectively, depict a plumbing diagram for the recirculating fluidic delivery system and its equivalent lumped-element electric circuit schematic. FIG. 3B depicts a schematic diagram for the system 40, with the addition of a pressure gauge 52. The pressure gauge 52 is connected to the feed leg of a hollow member, which comprises two sections of differing diameter 54 and 56. The return leg of the hollow member comprises the two sections of differing diameter 58 and 60. The hollow member connects through a T-junction 62 to the cannula 46. As depicted, any or each of the sections of the hollow member may have a different diameter than the cannula 46. FIG. 3C depicts a circuit representation of the system of FIG. 3B. Here, the resistance of each hollow member section 54, 56, 58, and 60 is shown, along with the resistance within the cannula 46 and the capacitance in the feed and return legs 64 and 66.

By careful selection of the geometric properties of the cannula 46 and hollow member sections 54, 56, 58, and 60, the flow pattern properties within the system and the resulting drug delivery rates to the cochlea 48 can be controlled. In a particular embodiment of the invention, selection of the systems geometric properties and the operation properties of the micropump 44 can produce a reciprocating flow within the system. In this configuration, the fluid capacitance and fluid resistance within the delivery system can be selected and, optionally, controllably altered to provide an oscillating flow through a single cannula 46. This flow regime can have a number of important benefits, such as, but not limited to, improving mixing of the drug and perilymph within the delivery system and cochlea 48, carefully controlling the rate of drug delivery to the cochlea 48, and helping to avoid occlusion within the tubing. This configuration also allows for a transport of fluid into and out of the cochlea 48 using only a single interface member. In other embodiments, as described below, the properties of the hollow member and the cannula 46 are selected so that the hollow member and the cannula 46 fill with fluid (e.g., withdraw fluid from a bodily cavity of an organism) at a different rate than the rate at which fluid empties from the hollow member and the cannula 46 (e.g., discharges into the bodily cavity of the organism). For example, the properties of the hollow member and the cannula 46 may be selected to make the emptying rate higher than the filling rate, or vice versa.

In some embodiments, the micropump driving the fluid is a reciprocating solenoid pump (such as a Wilson Greatbatch WGL 05) with a 0.5 uL fixed stroke volume operating up to 20 psi. The transition time of the pump stroke is preferably much smaller than the pump cycle time, which is 0.33 sec minimum (3 Hz maximum pumping frequency). The nominal feed and return tubing between the pump and T-junction are each approximately 50 cm long with negligible resistance, having an I.D. of 1.0 mm. These tubes may function as the primary source of compliance (CF and CR described below) and could vary in material from silicone (modulus ~10 MPa) to PEEK (modulus 1 GPa). The T-junction capillaries are rigid (fused silica). The tubes represented by RFT and RRT should have I.D. less than 250 um (not necessarily equal) and length of at least 10 mm. The cannula 46 is assumed fixed, because of surgical constraints, with I.D. 75 um and length 20 mm.

To satisfy the above condition, one half of a flow cycle must generate a fluid flow volume of at least that of the mixing tube volume.

$$V_M = \frac{\pi}{4} \cdot D_{IM}^2 \cdot L_M = 0.088 \text{ uL} \qquad \text{(Formula 1)}$$

Given the circuit configuration, it is difficult to achieve this without some capacitance in the system. Specifically, with the fluidic capacitors shown in FIG. 3C removed, there is no loop that includes the mixing output leg RM through which fluid can flow. Equivalently, there is no storage capability in the pump loop which allows fluid to be stored in such a way that the flow rates in the T-feed and T-return sections can be unequal at the same instant in time, which is the only condition under which fluid may flow in the cannula.

In one embodiment of the fluidic delivery system described with reference to FIGS. 3A-3C, the micropump can be configured to operate continuously at a predetermined frequency. In a second embodiment, the micropump input can be modulated so that it periodically turns on and off at some frequency much lower than the pump cycle frequency, and also more slowly than the largest system time constant, thereby operating non-continuously.

In order to analyze the system described in FIGS. 3A to 3C, a number of system parameters must be calculated for the component geometry and properties, and a number of simplifying approximations must be made. For example, the pump pulse time is estimated to be of the order of milliseconds. Also, the resistance to fluid flow of a tube with circular and constant cross section can be given by:

$$R = \frac{128 \cdot \eta \cdot L}{\pi \cdot D_I^4} \quad \text{(Formula 2)}$$

where η is the dynamic viscosity, L is the tube length, and $D_I$ is the tube inner diameter.

For an expandable piece of tubing, the capacity to store fluid can be approximated by:

$$C = \frac{dV}{dP} = \frac{\pi \cdot L \cdot D_I^3}{2 \cdot E_Y \cdot (D_O - D_I)} \quad \text{(Formula 3)}$$

where $E_Y$ is the elastic modulus, $D_O$ is the outer diameter, and $D_I$ again refers to the tube inner diameter. Alternatively, to use the compressibility of a length of air bubble in a portion of tubing, the capacitance can be described approximately by:

$$C = \frac{L_0 \cdot \pi \cdot D_I^2 \cdot P_0}{4 \cdot P^2} \quad \text{(Formula 4)}$$

where $L_0$ is the length of the bubble when at pressure $P_0$, and P is the bubble pressure. It should be noted that this expression describes a non-linear element (i.e., it is dependent on the pressure). For analysis, the average pressure of the bubble (i.e., $P=P_{avg}$) gives reasonably accurate estimates of the bubble capacity as long as the average is large compared to its maximum deviation from that average.

Laplace domain analysis of the circuit in FIGS. 3A-3C yields the transfer function:

$$\frac{I_0}{I_S} = \frac{-A_0 \cdot \omega_n^2 \cdot s}{(s^2 + 2 \cdot \zeta \cdot \omega_n \cdot s + \omega_n^2)} = \frac{-A_0 \cdot \omega_n^2 \cdot s}{(s + \omega_H) \cdot (s + \omega_L)} \quad \text{(Formula 5)}$$

where $I_0$ is the fluid flow through the output tube, $I_S$ is the source flow, and the system gain, undamped natural frequency, damping ratio, and high and low frequency poles are given respectively by:

$$A_0 = R_{FT} \cdot C_F - R_{RT} \cdot C_R \quad \text{(Formula 6)}$$

$$\omega_n = [C_F \cdot C_R \cdot (R_{FT} \cdot R_{RT} + R_{FT} \cdot R_M + R_M \cdot R_{RT})]^{-\frac{1}{2}} \quad \text{(Formula 7)}$$

$$\zeta = \frac{\omega_n \cdot (R_M \cdot C_R + R_{FT} \cdot C_F + R_{RT} \cdot C_R + R_M \cdot C_F)}{2} \quad \text{(Formula 8)}$$

$$\omega_H = \left(\zeta + \sqrt{\zeta^2 - 1}\right) \cdot \omega_n \quad \omega_L = \left(\zeta - \sqrt{\zeta^2 - 1}\right) \cdot \omega_n \quad \text{(Formula 9)}$$

It can be shown, by taking partial derivates of Formula (8) with respect to the various circuit elements, that the damping ratio ζ for this system is always greater than or equal to one, and in fact is only equal to one in two trivial non-useful scenarios, and thus the system never has an under-damped, decaying-oscillation response to an impulse or unit step input.

FIG. 4A depicts a qualitative plot of the pump flow output for the configuration where the micropump is configured to operate continuously at a predetermined frequency. Here, the cycle frequency is 1 Hz and the pulse time is 0.05 sec. In this operating mode, the system design time constants are large compared to the pulse time but small compared to the pump cycle period. As a result, the input can be modeled as an impulse function. A single pulse of the pump would be expected to generate a transient flow event such that the total volume exchange during that event would exceed that given by the above stated Formula (1).

The volume impulse response is given by:

$$V_{imp} = \frac{V_{stroke} A_0 \cdot \omega_n}{2 \cdot \sqrt{\zeta^2 - 1}} \cdot (\exp(-\omega_H \cdot t) - \exp(\omega_L \cdot t)) \quad \text{(Formula 10)}$$

where, as mentioned above, it is assumed that the stroke volume is delivered in a time interval small compared to all system time constants. This results in a maximum volume exchange of $$V_{cycl} = \frac{V_{stroke} A_0 \cdot \omega_n}{2 \cdot \sqrt{\zeta^2 - 1}} \cdot \left[\left(\frac{\omega_H}{\omega_L}\right)^{\frac{\omega_H}{\omega_L - \omega_H}} - \left(\frac{\omega_H}{\omega_L}\right)^{\frac{\omega_L}{\omega_L - \omega_H}}\right] \quad \text{(Formula 11)}$$

The maximum flow rate produced within the mixer tube, which occurs at t=0, is given by:

$$I_{imp\_max} = \frac{-V_{stroke} A_0 \cdot \omega_n \cdot (\omega_H - \omega_L)}{2 \cdot \sqrt{\zeta^2 - 1}} \quad \text{(Formula 12)}$$

Control of the performance characteristics of the device can be achieved by careful selection of the parameters of the device. Design inputs, such as, but not limited to, the inner and outer diameters of the tubing in the double-lumen catheter and the cannula interfacing with the body cavity, the pump frequency, and the stroke volume may be set to produce the performance characteristics required for a given design.

Example data for two sets of design inputs, specifically for an example high flow and low flow configuration, can be seen in FIGS. 5A and 5B. The relevant input data and calculations can be found in the spreadsheet of FIGS. 7A-7B. In each case, the stroke volume was set to 0.5 uL. It can be seen from the results that the high flow configuration exchanges about three times the mixer tube volume, while the low flow configuration exchanges a volume approximately equal to that of the mixer tube. It should be noted that the flow rates vary substantially with time. For example, in the high flow configuration, the system draws 0.22 uL into the system in approximately 10 sec, but takes approximately 1.5 min to fully expel it. By setting the device to operate continuously at a predetermined frequency, a relatively small exchange volume (only several times that of the mixer tube volume) and flow rates is possible. Also, the pump frequency should be slow compared to $\omega_L$. The calculations used in the spreadsheet of FIGS. 7A-7B calculates a pump frequency which is 3 times slower than $\omega_L$. This margin can be adjusted depending on the desired pumping characteristics.

In an alternative embodiment of the invention, the micropump input can be modulated so that it periodically turns on and off at a frequency much lower than the pump cycle frequency, and also more slowly than the largest system time constant. In this operating mode, the system time constants are large relative to both the pulse time and the pump cycle period. As a result, the pump effectively looks like a constant current (flow) source rather than a pulse train, as can be seen in FIG. 4B, which depicts a qualitative plot of the pump flow output with respect to time. The resulting flow rate in this configuration is given by:

$$I_{S0}=V_{stroke} \cdot f_p \quad \text{(Formula 13)}$$

where $V_{stroke}$ is the pump's stroke volume and $f_p$ the pump frequency. In this case, the pump is modeled as a step function current (flow) source, again, assuming it is left "on" longer than the longest system time constant.

The step input in Laplace domain is given by $$I_S = \frac{I_{S0}}{s},$$

so Formula (5) becomes:

$$\frac{I_{us}}{I_{S0}} = \frac{-A_0 \cdot \omega_n^2}{(s^2 + 2 \cdot \zeta \cdot \omega_n \cdot s + \omega_n^2)} \quad \text{(Formula 14)}$$

and the time domain step response is:

$$I_{us} = \frac{-I_{S0} A_0 \cdot \omega_n}{2 \cdot \sqrt{\zeta^2 - 1}} \cdot (\exp(-\omega_L \cdot t) - \exp(-\omega_H \cdot t)) \quad \text{(Formula 15)}$$

where $I_{S0}$ is the pump flow rate amplitude. The time dependent response approaches zero for large time, due to the decaying exponentials. Its integral, the fluid volume, is given by:

$$V_{us} = \frac{-I_{S0} \cdot A_0 \cdot \omega_n}{2 \cdot \sqrt{\zeta^2 - 1}} \cdot \left( \frac{\exp(-\omega_H \cdot t)}{\omega_H} - \frac{\exp(-\omega_L \cdot t)}{\omega_L} + \frac{2 \cdot \sqrt{\zeta^2 - 1}}{\omega_n} \right) \quad \text{(Formula 16)}$$

which asymptotically approaches a constant value, given by:

$$V\text{cycus}=-I_{S0} \cdot A_0 \quad \text{(Formula 17)}$$

As in the cases with a continuously operating micropump, the maximum flow rate in this configuration is critical to the design, and is given by:

$$I_{us\_max} = \frac{-I_{S0} A_0 \cdot \omega_n}{2 \cdot \sqrt{\zeta^2 - 1}} \cdot \left[ \left(\frac{\omega_L}{\omega_H}\right)^{\frac{\omega_L}{\omega_H - \omega_L}} - \left(\frac{\omega_L}{\omega_H}\right)^{\frac{\omega_H}{\omega_H - \omega_L}} \right] \quad \text{(Formula 18)}$$

Figure 6A:
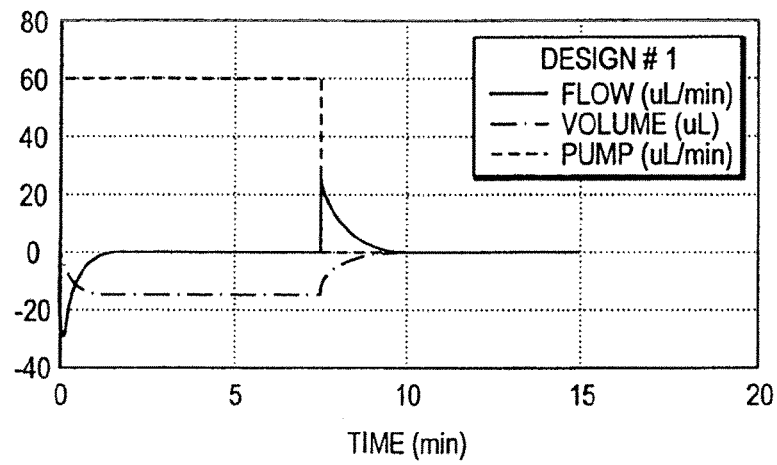
FIG. 6A is a plot of an example output flow for one example delivery system design with a pump which is periodically turned on and off at a frequency lower than the pump cycle frequency, in accordance with one embodiment of the invention.
Figure 6B:
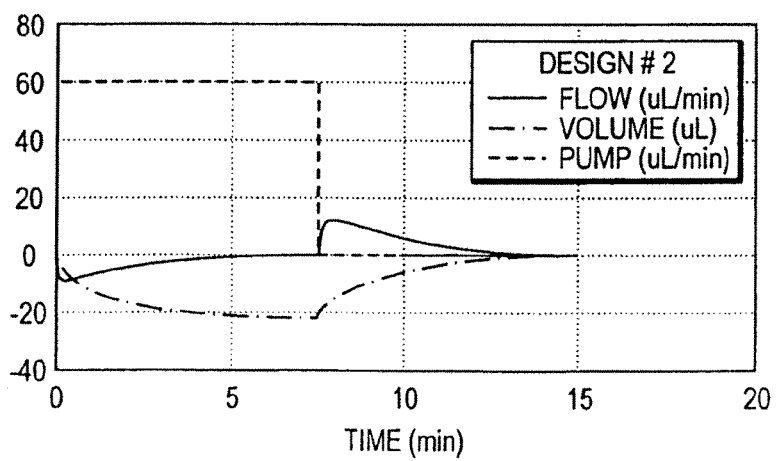
FIG. 6B is a plot of a second example output flow for one example delivery system design with a pump which is periodically turned on and off at a frequency lower than the pump cycle frequency, in accordance with one embodiment of the invention.

Predicted output data for the configuration where the micropump input is modulated can be seen in FIGS. 6A and 6B. Again, data is shown for two sets of design inputs, specifically for an example low flow and high flow configuration. The high flow case, shown in FIG. 6B, clearly generates a larger volume exchange, but because of the larger system time constants, has a lower maximum flow rate than the lower flow configuration. In this case, the larger capacitances more than compensate for the reductions in feed resistances in producing larger time constants and system gain $A_0$. In using the embodiment where the micropump input is modulated, it should be noted that the volume exchanges shown will be achieved only if the modulation time is large relative to the slowest time constant.

In choosing system components to optimize performance, it should be noted that the maximum pressure developed at the pump is given by:

$$P_{max}=I_{S0} \cdot (R_{FT}+R_{RT}+R_F+R_R) \quad \text{(Formula 19)}$$

Thus, it is important to choose component values carefully such that the pump will perform properly. It should be noted that in each of the above example embodiments only the primary feed and return lines were assumed to have sufficient compliance to contribute significantly to the capacitance in the system. The elastic modulus used in the calculations was 11 MPa.

It can be seen that by modulating the micropump input, substantially larger exchange volumes and flow rates are possible than for the examples where the micropump operates continuously at a predetermined frequency. The pump frequency is used to set the average flow rate. The exchange volume and flow rate are directly proportional to this average flow rate and thus the pump frequency. It should be noted that the equations and example data shown here are only accurate for cases where the pump frequency is not comparable to $\omega_L$. Specifically, the error is 10% at $f_p=2\omega_L$ and will increase as $f_p$ is decreased. Further, the pump on-off modulation frequency should be slow compared to $\omega_L$. The example data is calculated for a pump modulation frequency which is three times slower than $\omega_L$. This margin can be adjusted depending on the desired pumping characteristics.

A possible disadvantage of the embodiments of the drug delivery apparatus described above with reference to FIGS. 2A-2B and 3A-3C is its sensitivity to tubing dimensions, which may change over time. Additionally, a micropump employed by the apparatus according to those embodiments should be biocompatible and suitable for pumping biological fluids. Accordingly, in alternative embodiments, instead of a circulating fluid loop, a flexible diaphragm or slidable piston in contact with a working chamber facilitates reciprocating flow through the cannula and into and out of the body organ, simplifying implementation of the drug delivery apparatus as a microfabricated system and improving its resistance to biological fouling.

Figure 8A:
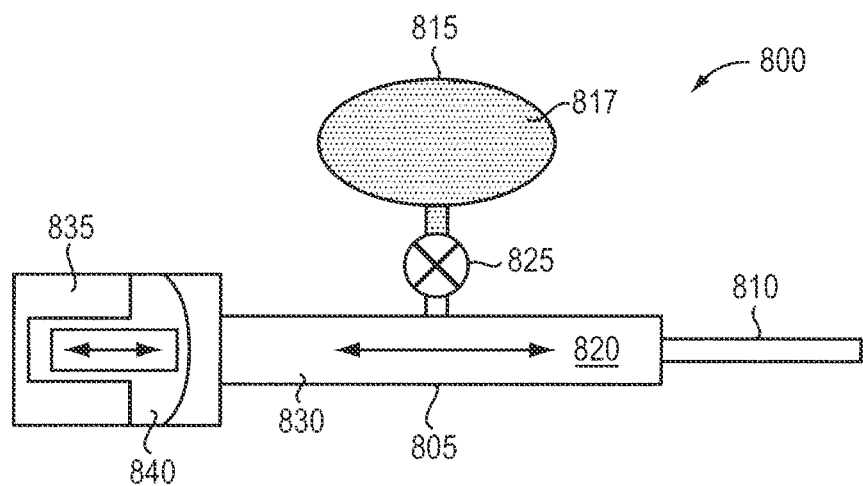
FIGS. 8A-8B are schematic views of a drug delivery apparatus in accordance with alternative embodiments of the invention.
Figure 8B:
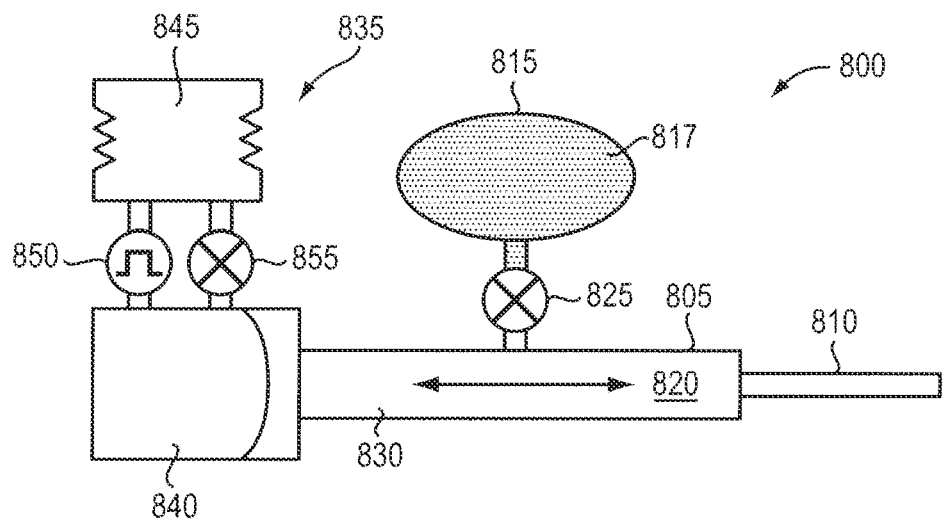

In particular, referring to FIGS. 8A and 8B, in some embodiments, a drug delivery apparatus 800 includes a variable-volume vessel (or hollow member) 805 and an interface member 810, for example a cannula. The apparatus may also include a reservoir member/drug storage element 815 for storing a drug 817. The vessel 805 has a variable-volume working chamber 820 in fluid communication with the interface member 810 and the reservoir member 815, if one is used by the apparatus. The reservoir member 815 is separated from the chamber 820 by a valve 825. The working chamber 820 contains a therapeutic fluid 830, including the drug and, in operation, a certain amount of bodily fluid, for example perilymph. The apparatus further includes an actuator 835 for varying the pressure within the working chamber 820 by altering its volume. For example, in many versions of these embodiments, the actuator 835 periodically increases and decreases the volume of the chamber 820 by either deflecting or slidably moving at least a portion of at least one wall of the vessel 805. In some versions, either an entire wall 840 of the vessel 805, or a portion thereof, includes a flexible membrane or diaphragm, as shown in FIGS. 8A and 8B. In other versions of these embodiments, the vessel 805 has a slidably movable wall. The motion of the wall 840 could be produced by a mechanical actuator, such as a miniature electromagnetic actuator disclosed in co-pending patent application Ser. No. 11/169,211 entitled "Electromagnetically-Actuated Microfluidic Flow Regulators and Related Applications" and incorporated herein by reference in its entirety. Alternatively, the wall motion could be produced by fluid pressure from a conventional pneumatic or hydraulic apparatus, for example as shown in FIG. 8B, employing a working fluid or gas 845, a pump 850, and a valve 855. Other configurations of the vessel 805 that vary the pressure within the working chamber 820 by altering its volume are also contemplated. The hollow member 805 may also have sections of different diameters, some or none of which may be the same as a diameter of the cannula 810.

In operation, in a similar fashion to the embodiments described above with reference to FIGS. 2A-2B and 3A-3C, the interface member 810, for example a cannula, is brought into contact with a desired bodily cavity of a patient, for example a cochlea of a human ear, in order to periodically deliver the therapeutic fluid to and draw bodily fluid from the bodily cavity. At desired (sometimes non-continuous) intervals, the actuator 835 causes the wall 840 or a portion thereof to move or deflect inward, reducing the volume of the chamber 820 and causing therapeutic fluid 830 to flow, at a discharge rate, from the chamber 820 and the hollow member 805 through the cannula 810 (and a lumen thereof) into the patient's bodily cavity. The wall 840 may be temporarily maintained by the actuator 835 in this inward position. At opposing intervals, the wall 840 or a portion thereof moves or deflects in the opposite direction, causing bodily fluid to flow at a draw rate from the patient's bodily cavity through the cannula 810 (and a lumen thereof) to the chamber 820 and hollow member 805. This opposite motion may occur at a different rate than the inward motion, and the draw rate may thus be different than the discharge rate. Thus, composition of the therapeutic fluid, including concentration of the drug 817 therein, varies during its recirculation through the working chamber 820. At other intervals, which may or may not be synchronized with or coupled to the periodic motion of the wall 840, the reservoir 815 releases drug compounds to be mixed with the bodily fluid in the chamber 820. Alternatively, pressure variation in the working chamber 820 due to the motion of wall 840 could be used in a mechanism for dispensing drug 817 from the reservoir 815. For example, synchronized operation of the reservoir valve 825 with the low-pressure phase in the chamber 820 could cause dispensation of the drug 817.

Similarly to the embodiments described above with reference to FIGS. 2A-2B and 3A-3C, the apparatus may also include a regulating system and/or a control system in communication with the vessel 805, the actuator 835, and/or the reservoir 815 for monitoring and maintaining a desirable drug delivery rate and/or controlling a flow pattern of the fluids through the working chamber 820. For example, fluid may be caused to empty from the hollow member 805 and the cannula 810 at a higher rate than the rate at which fluid is withdrawn from the patient's bodily cavity. Flow patterns may also be controlled with the inclusion of a compliant element adapted to act as a fluidic capacitor as part of the hollow member 805. Other operation procedures may involve modulating the actuator 835 to turn on and off at a frequency lower than an actuator cycle frequency. Further, the variable-volume vessel 805 and the actuator 835 can be shaped and dimensioned to fit within a desired bodily cavity, for example, a mastoid cavity of a human.

Additional embodiments of the device may include advanced flow regulating elements, actuation mechanisms, and/or drug storage/release configurations. These features may be employed to improve power efficiency, reliability, regulation of the flow rate, and/or the introduction of drugs to a flowing liquid. For example, the reciprocating flow need not necessarily be continuous. In order to conserve power, prolong the mechanical life of the device, and/or maximize transport by diffusion, the infuse and withdraw actions may be separated by idle segments of time.

Additionally, the flow rates for the infuse phase and the withdraw phase need not be identical, although the net infuse volume and net withdraw volume may always nearly be equal. For example, a flow cycle with a rapid infuse phase (lasting approximately 5 to 10 seconds, with a peak flow rate of approximately 10 µL/min), a dwell time of approximately a few seconds, a slow withdraw phase (lasting approximately 20 to 60 seconds, with a peak flow rate of approximately 3 µL/min), and an idle phase lasting approximately several minutes may be employed. When operating under these parameters, approximately 0.5 to 1 µL may be infused and withdrawn.

Several competing factors may be considered when selecting the system parameters, including the effectiveness of mass transport, the mechanics of the actuation mechanism, the safety of the therapy, the interaction of the drug with tissue and endogenous fluid, and the total displaced volume desired. Different embodiments of a drug release mechanism may introduce additional conditions into the flow cycle. Thus, the optimized parameters for each embodiment may vary, depending upon the device configuration and therapeutic protocol.

A specific example of such optimization prioritizes improving transport of the drug to remote regions of the organ. In the case of the cochlea, and particularly the scala tympani, a surgical procedure may require placing the cannula outlet at the base (basal turn) of the organ. Ideally, the delivered drug will reach all tissues of the organ, but the cochlea's tapering and helical shape can inhibit transport to the apex of the organ. Accordingly, a reciprocating delivery may be employed to distribute the drug into a volume in the base of the cochlea, while the distribution of the drug throughout the rest of the cochlea occurs by diffusion. The flow rate may be increased in order to distribute the drug into a larger volume that extends more apically. Over short time courses (e.g., less than approximately 2 hours), the apical extension, though small, may significantly enhance apical delivery of the drug. Over longer time courses (e.g., greater than approximately 5 hours) or greater distances (e.g., greater than approximately 3 mm), maintenance of drug concentration in the basal scala tympani may prove more advantageous for extending apical delivery than increases in flow rate.

Non-symmetric and non-continuous flow profiles may also be obtained in a small, low-power format through variations on a simple reciprocating actuator. As previously described, reciprocating flow patterns may be achieved through an elastic membrane or bellows that is compressed to provide the infuse phase of flow. The component may relax passively to provide the withdraw phase. This may be achieved by using, for example, a polyimide membrane (approximately 6 to 8 mm in diameter, and approximately 125 µm thick) in an otherwise rigid cavity, and a miniature commercial solenoid actuator to displace the membrane. Alternatively, the component may relax passively to provide the infuse phase. These approaches may be further refined to allow more control over the flow parameters. For example, resistive, capacitive (mechanically compliant), and/or rectifying components may be introduced into the flow path between the compressed element and the outlet, such as introducing an orifice or small tube to reduce flow rates generated by the actuator.

Figure 9:
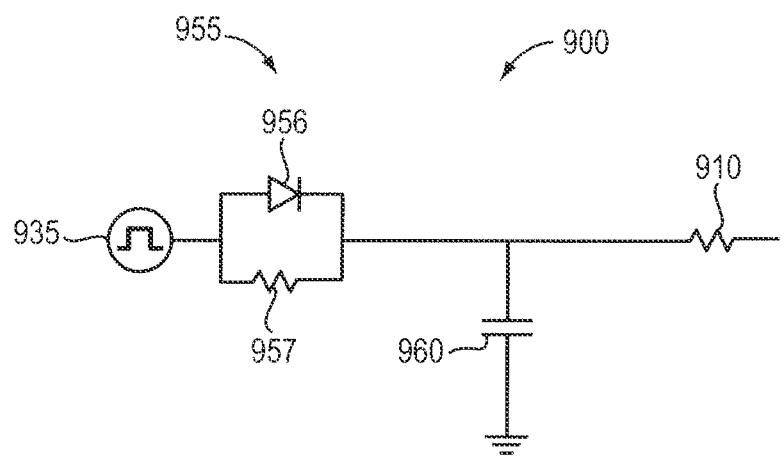
FIG. 9 is a schematic diagram of a drug delivery apparatus, in accordance with another embodiment of the invention.

FIG. 9 depicts schematically (with electrical analogues) a drug delivery apparatus 900 with an actuator 935, a leaky check valve 955, a capacitor 960, and an outlet cannula 910, to convert a rapid, symmetric actuator stroke into a slower infuse flow and an even slower withdraw flow (i.e., an asymmetric infuse and withdraw flow with increased time constants over the time constant of the actuator 935). The apparatus 900 may also include a hollow member defining a lumen that may fluidically communicate with the cannula 910, and, in some embodiments, a drug storage element. The actuator 935 may be one of a variety of actuators capable of creating flow through the apparatus 900 via the hollow member and/or the cannula 910, such as a reciprocating membrane coupled to a motor. The actuator 935 may be selected for its properties to match the desired flow, and may also be used to modulate the source flow. For example, a working chamber (or other interface between the actuator 935 and the drug) may be compressed by a linear motor, a rotating motor with a cam configuration, or a solenoid/electromagnet that has latching or other bistable modes so that it can hold the chamber in the compressed state with minimal or zero power being used. Alternatively, any of the above devices may be used in an inverse setup, so that rather than compressing the membrane, the actuator 935 causes the withdraw phase of flow and the infuse phase is passive. The actuator 935 does not always need to be in operation, and in many cases is adapted to operate non-continuously.

The leaky check valve 955 may be modeled as a one-way check valve 956 in parallel with a resistive element 957, indicating that though flow is primarily one-way across the leaky check valve 955 (either through the one-way check valve 956 alone or in combination with the resistive element 957, such as a smaller diameter cannula, representing a leak path), it is possible for flow to go in the opposite direction across the resistive element 957. The check valve 955 may be located within the cannula 910 or the hollow member. The capacitor 960 may be a flexible diaphragm, with its dimensions selected such that it is deflected to a desired degree by pressure values induced during reciprocating flow. The diaphragm may be one portion of a wall of the lumen.

The cannula 910 may be the same or similar as those previously described with respect to other embodiments. The cannula 910 may facilitate fluid flow through a lumen thereof, for flow both to and from a bodily cavity. To deliver drug, the hollow member and/or the cannula 910 may be filled with fluid at a first rate, which then empties from the hollow member and/or the cannula 910 at a second rate different from the first rate.

Methods of releasing drug into the carrier fluid may differ depending on the selected drug(s), the drug stability, and/or the duration of the therapy, amongst other factors. Several embodiments with a pressurized drug reservoir, which is isolated from the carrier fluid by a valve and injected into the carrier fluid upon activation of a valve, have been described.

There are several alternatives for releasing drug from the drug storage element. In one embodiment, a wetted interior of the device and/or cannula can be coated with "controlled release" or an erodible solid or polymer configuration, so that drug is continuously and passively released into the reciprocating fluid. In another embodiment, rather than a single reservoir and valve, the drug storage element has multiple compartments containing dry or liquid drug, each separated by a single-use valve from the hollow member, allowing each valve to be individually or jointly activated to release drug in discrete doses. The drug storage element may be configured to release multiple compounds, each at different time points, according to a specific therapeutic sequence. In some embodiments, a second actuator may be used to deliver drug.

In many cases, it is desirable to insert drug (referred to as "loading") into a channel while producing substantially negligible, or zero, flow at an outlet of the channel. Negligible may be characterized as a volume much less than the volume of drug loaded into the channel. This may be aided by using a cannula, disposed at the end of the channel, having a greater flow resistance than other aspects of the device, such as a cannula with a smaller inner diameter than the other components, in conjunction with the further features described below (e.g., a waste reservoir 1016 or a dosing pump 1165). For example, the cannula may have an inner diameter of approximately 75 microns, while the channel may have an inner diameter of approximately 200-300 microns.

Loading drug while producing little or no flow at the outlet helps provide a greater degree of control over the operation of the system. For example, an operator can deliver the same average drug volume as, but with higher peak flow rates than, a more common constant flow device that delivers drug at a slow and steady rate and at a fixed concentration. A human cochlea may be able to safely receive infusion rates up to approximately 10 µL/min of fluid, although the actual number may vary based on the individual and the drug being delivered. A human cochlea may also be able to safely receive a total fluid volume of approximately 3 µL over a period of 1 hr, though again this limit may be higher or lower with respect to the individual and/or the specific therapy.

Higher peak flow rates may be used to prevent or reverse occlusion, especially that as might occur from biofouling. Often, there may be a build up of protein that can be removed with a higher flow, particularly a pulsed flow. As reciprocating flow in the device may be controlled differently at different phases (e.g., drug loading, discharge, and withdraw), a particularly high flow, low volume pulse may be used to unclog components (e.g., the channel or the cannula) without disturbing a desired dosage protocol. The flow rate of this pulse may rise and fall rapidly. Controlling an actuator driving the flow also allows for optimized delivery with desired pharmacokinetics (e.g., ensuring sufficient mixing and diffusion distances), while keeping the device parameters (e.g., flow, volume) within a safe range to avoid cell damage. This is not commonly achievable in existing devices, which tend to be limited as either passive systems or as systems that are restricted to constant control stroke lengths and/or speeds. Various embodiments of the device may include some or all of these features, as well as the features that follow.

Figure 10A:
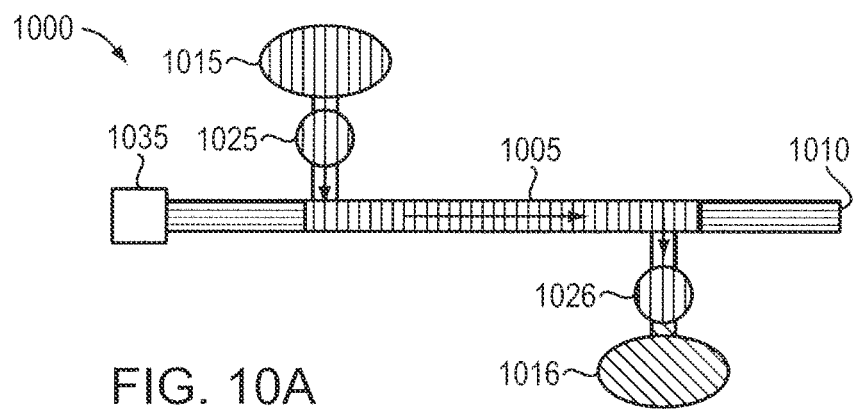
FIGS. 10A-10C depict schematic views of a drug delivery apparatus in various stages of operation, in accordance with yet another embodiment of the invention.
Figure 10B:
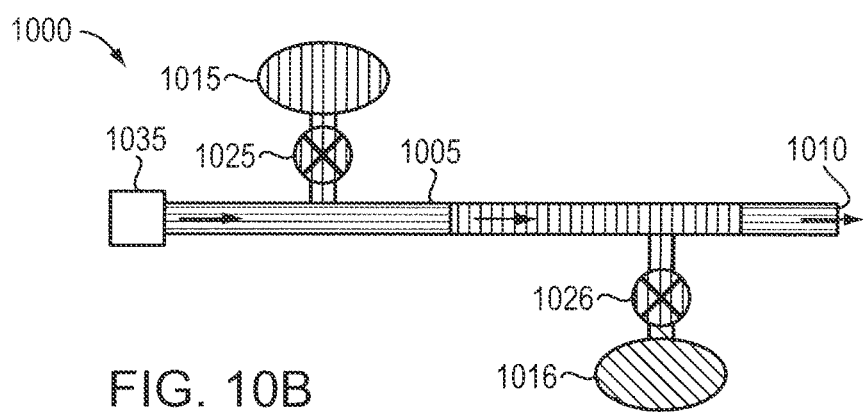
Figure 10C:
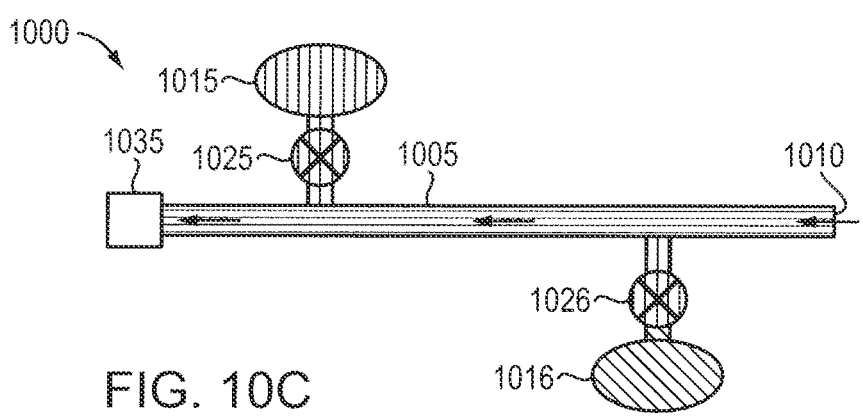

In some embodiments, such as the drug delivery apparatus 1000 depicted in FIGS. 10A-10C, drug may be injected into a channel (or hollow member) 1005 as a slug, as opposed to being mixed within the device. This allows the drug to be propelled into the organ with controllable dilution. The apparatus 1000 may also have a drug supply reservoir 1015 fluidically coupled to the channel 1005, such as via a drug supply valve 1025, an actuator 1035 for causing drug and/or carrier fluid flow through the channel 1005, a channel outlet 1010 for facilitating fluid flow through a lumen thereof to and from a bodily cavity, and a control system for controlling the actuator 1035 and the drug supply valve 1025 to deliver drug to the bodily cavity. A cannula may form part of the channel 1005, for example at a distal end thereof, such that a cannula outlet is coterminus with the channel outlet 1010. The control system may be configured to deliver drug in a substantially undiluted form. In some embodiments, the apparatus 1000 also includes a waste reservoir 1016 fluidically coupled to the channel 1005 via a waste reservoir valve 1026. The waste reservoir 1016 typically receives carrier fluid, as further described below, but may also receive carrier fluid mixed with drug, or even undiluted drug. The waste reservoir valve 1026 may also be controlled by the control system. The drug supply reservoir 1015 may be any of a number of structures suitable for holding a fluid, including a pressurized reservoir.

In operation, as depicted in FIG. 10A, the drug supply valve 1025 is opened to allow drug to empty from the drug supply reservoir 1015 into the channel 1005. In some embodiments, drug may be driven from the drug supply reservoir 1015 by a second actuator. At substantially the same time, the waste reservoir valve 1026 may be opened to allow carrier fluid in the channel 1005 to be received in the waste reservoir 1016. In a further refinement of this approach, the drug displaces an equal volume of carrier fluid in the apparatus 1000, such that the loading of drug does not generate any flow, or produces negligible flow, at the channel (or cannula) outlet 1010. As depicted in FIG. 10B, once a desired amount of drug has been loaded, the drug supply valve 1025 (sometimes along with the waste reservoir valve 1026) may be closed and the actuator 1035 activated to begin an infuse flow where drug is delivered to the bodily cavity. The desired amount of drug loaded may be greater than the amount to be delivered to account for dilution or other loss (e.g., to the waste reservoir 1036). In some embodiments, at least part of the infuse flow may occur with one or more of the valves 1025 and 1026 in an open position, thereby collecting excess carrier fluid in the waste reservoir 1016 as the carrier fluid flows toward the outlet 1010, though the waste reservoir valve 1026 is typically closed prior to drug entering the waste reservoir 1016, and typically even before activation of the actuator 1035. Carrier fluid may be delivered to the bodily cavity along with drug. Once the drug has been delivered to the bodily cavity via the outlet 1010, the actuator 1035 may reverse to start a withdraw cycle where carrier fluid is pulled back toward the actuator 1035 and the apparatus 1000 is readied for delivering another dose of drug, as shown in FIG. 10C.

Sometimes, the valves 1025, 1026 may simply be open junctions with fixed dimensions to control flow and the reservoirs 1015, 1016 may occupy the same volume. In such an embodiment, the control system may control a pump that incrementally circulates drug from the reservoirs 1015, 1016 through the channel 1005 and back into the reservoirs 1015, 1016 to refresh the load of drug in the channel 1005. Dimensioning of the junctions may help control the rate of fluid flow into and out of the reservoirs 1015, 1016, and the junctions may be differently sized to provide different discharge and draw rates.

Figure 11A:
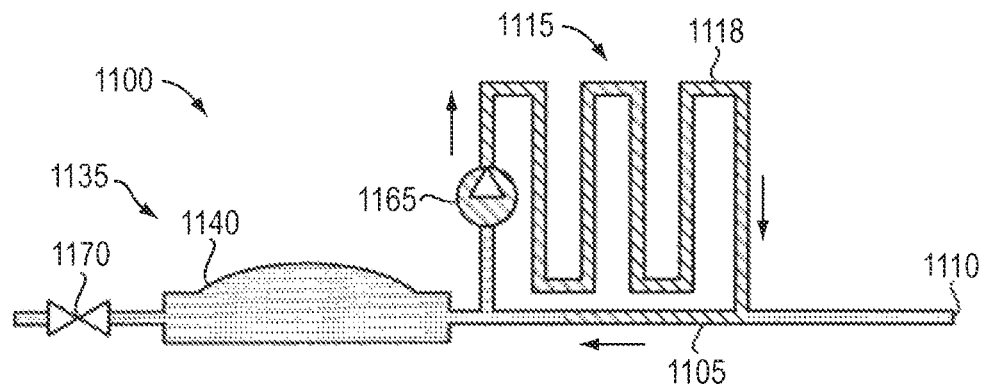
FIGS. 11A and 11B depict schematic views of a drug delivery apparatus in a loading cycle and a reciprocating cycle, respectively, in accordance with still another embodiment of the invention.
Figure 11B:
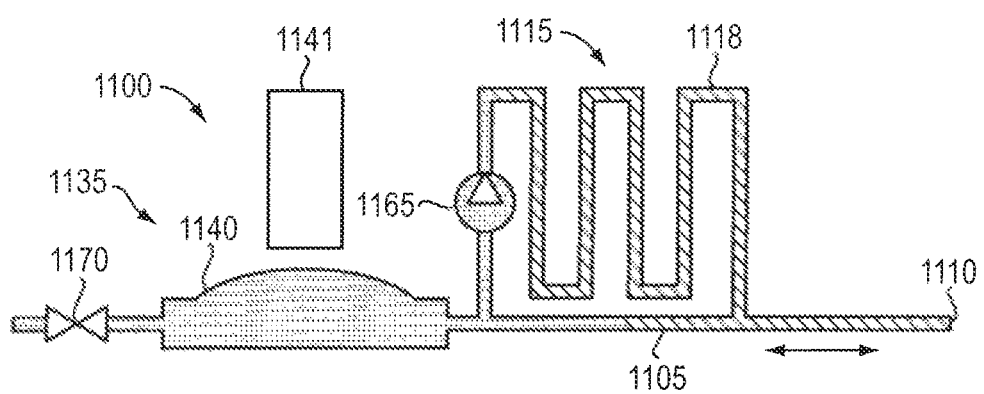

In other embodiments, as depicted in FIGS. 11A and 11B, a drug supply apparatus 1100 includes a second actuator (e.g., a drug dosing pump) 1165, in addition to other similar components as described above, such as an actuator 1135, a delivery channel 1105, a drug supply reservoir 1115, and an outlet 1110 defining a lumen for fluid to flow through, both to and from the bodily cavity. A cannula, such as a high flow resistance cannula as described above, may form part of the delivery channel 1105, for example at a distal end thereof so that an outlet of the cannula and the channel outlet 1110 coincide. The actuator 1135 may include a reciprocating membrane 1140 and a microactuator 1141 (such as a piston) to compress and release the membrane 1140, thereby causing flow in the delivery channel 1105. A priming valve 1170 may also be part of the apparatus 1100 to allow priming of the device prior to use.

The dosing pump 1165, which may be, as illustrated, located within the drug supply reservoir 1115, may operate independently from the actuator (or reciprocating flow mechanism) 1135, though it may operate to cause drug flow at a substantially similar rate to the rate at which the first actuator 1135 causes drug and carrier fluid flow. The dosing pump 1165 may meter drug within the device 1100 while the actuator 1135 causes the transfer of fluid from the apparatus 1100 to a patient. The dosing pump 1165 may also pull carrier fluid from the delivery channel 1105, which is particularly useful in limiting flow at the outlet 1110 to negligible amounts, or even zero, when loading drug into the delivery channel 1105. Several types of miniature or microscale pumps, such as, but not limited to, diaphragm pumps with piezoelectric or magnetically actuated membranes, mechanically driven peristaltic pumps, or electrokinetic pumps, may be used as the dosing pump 1165.

The dosing pump 1165 may prevent flow in the reverse direction (e.g., the direction opposite its usual direction of pumping), but not necessarily, especially when resistance in a flow path of the reservoir 1115 is significantly higher (e.g., approximately 10 times) than resistance in the delivery channel 1105. This may occur when the reservoir 1115 features a long, serpentine reservoir channel 1118. The reservoir channel 1118 may be of greater length than a length of the delivery channel 1105 and/or the cannula. For example, the reservoir channel 1118 may be approximately 30 cm long, while the delivery channel 1105 may be approximately 10 cm long (and the cannula portion thereof only approximately 2 cm long). Of course, these are only exemplary dimensions, and any of the components may be longer or shorter. The serpentine shape may be fabricated in a flat sheet of polyimide. This reservoir channel 1118 may have sufficient width and height (approximately 0.5 mm in one embodiment) to avoid significant resistive loading on the dosing pump 1165. The length of the reservoir channel 1118 may be much greater than its cross-section, including the height and width dimensions individually, so that diffusion is effectively limited to one dimension. In one embodiment, a reservoir channel 1118 having a width and a height of approximately 0.5 mm and a length of approximately 250 mm results in a reservoir volume of about 100 µL and may be fabricated in a flat sheet with dimensions of approximately 20 mm by 30 mm by 2 mm.

One-directional pumping, for example as may be implemented in the dosing pump 1165, may also be achieved in the reservoir channel 1118 using a microfabricated diaphragm and check valves. The check valves may be fabricated in polyimide, as is known in the art, and placed both upstream and downstream of a polyimide membrane in an integrated substrate. In one test, cyclically compressing and releasing the membrane pumped water in the range of approximately 25 nL to 150 nL per stroke, depending on the duration of the force applied to the membrane. The check valves used had diameters of approximately 2.4 mm, and the central chamber had a diameter of approximately 6 mm with a depth of approximately 0.4 mm.

When in operation, the dosing pump 1165 (either through a partial, single, or multiple strokes) may be activated to force the contents of the reservoir 1115 in a circulating loop, such that the reciprocating delivery channel 1105, or a portion of it, is loaded (known as the loading step) with a desired amount of drug at full concentration, as shown in FIG. 11A. At substantially the same time, carrier fluid from the delivery channel 1105 may be pulled into the reservoir 1115 by the dosing pump 1165, exchanging volumes so that flow out of the outlet 1110 is negligible, which may be aided at this stage with balanced resistances and pressures. Following loading, the dosing pump 1165 may be deactivated (sometimes after a single stroke) and the actuator 1135 may be activated to initiate a reciprocating cycle (see FIG. 11B), where drug is expelled into a delivery site (e.g., into a bodily cavity) and then withdrawn as a diluted mixture of endogenous fluid and drug via the outlet 1110, with negligible flow through the reservoir 1115. The flow through the reservoir may remain negligible by selecting a fluidic resistance significantly greater than a resistance of the delivery channel 1105, or by incorporation of a dosing pump 1165 that restricts flow when not activated, or by a combination of these approaches, amongst others. The volume of drug loaded may be substantially similar to the volume displaced by the reciprocating pulse, in some embodiments up to approximately 1 µL, and even greater. Much smaller discrete volumes (e.g., approximately 200 nL and lesser, or the volume of a single stroke) may be loaded and delivered if desired. Passive diffusion of residual fluid may reduce concentration of drug in the reservoir 1115 near junctions with the delivery channel 1105, and may be taken into account when analyzing and optimizing the design of the apparatus 1100.

Any one of the devices described above may be integrated with a cochlear prosthesis, such as one manufactured by Cochlear (Macquarie University, Australia), Med-EL (Durham, N.C.), or Advanced Bionics (Valencia, Calif.). The combined device may electrically stimulate the auditory system, while in some embodiments also delivering drugs to the cochlea to treat hearing disorders, to reduce the risk of side effects from implant surgery, and/or to improve performance of the prosthesis. Any one of the devices described above may also contain one or more sensors to measure and/or monitor physiological conditions of the patient. For example, the sensors may measure properties of the endogenous fluid that has entered the device.

Though the embodiments above are described for human patients, the device may be specifically configured for clinical studies involving animals and may be implanted completely or worn externally. Further, usage of the device in applications other than the treatment of auditory disorders, such as delivering drug to other organs where small controllable doses are required and where systemic delivery is impractical or harmful, is contemplated and considered within the scope of the invention.

The invention may be embodied in other specific forms without departing form the spirit or essential characteristics thereof. The foregoing embodiments, therefore, are to be considered in all respects illustrative rather than limiting on the invention described herein. Moreover, it is to be understood that the features of the various embodiments described herein were not mutually exclusive and can exist in various combinations and permutations, even if such combinations or permutations were not made express herein, without departing from the spirit and scope of the invention. Scope of the invention is thus indicated by the appended claims rather than by the foregoing description, and all changes that come within the meaning and range of equivalency of the claims are intended to be embraced therein.

What is claimed is:

1. A drug delivery apparatus for delivering a drug into a bodily fluid in a bodily cavity over a period of time, the apparatus comprising:
    a delivery channel, comprising an outlet, for facilitating fluid flow through a lumen thereof to and from the bodily cavity;
    a drug dosing actuator for loading a drug into the delivery channel, controlled independently of a second actuator, while producing negligible flow at the outlet; and
    the second actuator for driving the drug and a carrier fluid through the delivery channel, out the outlet, and into the bodily cavity.

2. The apparatus of claim 1, wherein the drug dosing actuator causes drug flow at a substantially similar rate to the rate at which the second actuator causes drug and carrier fluid flow.

3. The apparatus of claim 1 further comprising a sensor for measuring properties of an endogenous fluid that enters the apparatus.

4. The apparatus of claim 1, wherein the second actuator comprises a reciprocating membrane.

5. The apparatus of claim 1, wherein the means for loading drug into the delivery channel while producing substantially negligible flow at the outlet comprises a drug supply reservoir for holding the drug and a waste reservoir for receiving the carrier fluid, the drug supply reservoir fluidically coupled with the delivery channel via a drug supply valve and the waste reservoir fluidically coupled with the delivery channel via a waste valve.

6. The apparatus of claim 5, wherein the means for loading drug into the delivery channel while producing substantially negligible flow at the outlet further comprises a control system for controlling the drug supply valve, the waste valve, and the first actuator so as to deliver the drug to the bodily cavity with a controlled degree of dilution.

7. The apparatus of claim 5, wherein the drug supply reservoir is a pressurized reservoir.

8. The apparatus of claim 1, wherein the apparatus is adapted to be integrated with a cochlear prosthesis for electrically stimulating an auditory system.

9. The apparatus of claim 8, wherein the apparatus is adapted to deliver drugs to the cochlea to treat hearing disorders.

10. The apparatus of claim 8, wherein the apparatus is adapted to reduce side effects of implant surgery.

11. The apparatus of claim 8, wherein the apparatus is adapted to improve performance of the prosthesis.

12. The apparatus of claim 1, wherein the drug dosing actuator for loading drug into the delivery channel while producing substantially negligible flow at the outlet comprises (i) a reservoir in fluid communication with the delivery channel, and (ii) a dosing pump for driving the drug from the reservoir into the delivery channel and for pulling at least a portion of the carrier fluid out from the delivery channel and into the reservoir.

13. The apparatus of claim 12, wherein the reservoir is formed in a flat sheet of polyimide.

14. The apparatus of claim 12, wherein the dosing pump is configured to drive the drug in only one direction.

15. The apparatus of claim 12, wherein the dosing pump is configured to deliver at least 200 nL per stroke.

16. The apparatus of claim 12, wherein the reservoir comprises a reservoir channel of greater length than a length of the delivery channel.

17. The apparatus of claim 12, wherein the reservoir channel length is greater than both a width and a height of the reservoir channel.

18. A method for delivering a drug into a bodily fluid in a bodily cavity over a period of time, the method comprising:
    loading, using a dosing pump controlled independently of a second actuator, a drug from a drug supply reservoir into a delivery channel while producing negligible flow at an outlet of the delivery channel; and
    activating the second actuator to drive the drug and a carrier fluid through the delivery channel, out the outlet, and into the bodily cavity.

19. The method of claim 18 further comprising reversing the second actuator to reverse carrier fluid flow after delivery of the drug through the outlet.

20. The method of claim 18, wherein the drug supply reservoir is formed in a flat sheet of polyimide.

21. The method of claim 18, wherein the second actuator comprises a reciprocating membrane.

22. The method of claim 18, wherein the second actuator is activated so as to deliver a pulsed flow, thereby preventing or reversing occlusion of the delivery channel.

23. The method of claim 18, wherein loading the drug from the drug supply reservoir into the delivery channel while producing substantially negligible flow at the outlet of the delivery channel comprises:
   opening a drug supply valve to allow the drug from the drug supply reservoir to enter the delivery channel;
   opening a waste valve to allow at least a portion of the carrier fluid in the delivery channel to enter a waste reservoir;
   closing the drug supply valve after a desired amount of the drug has entered the delivery channel; and
   closing the waste valve prior to the drug entering the waste reservoir.

24. The method of claim 23, wherein a volume of the drug entering the delivery channel displaces an equal volume of the carrier fluid in the delivery channel into the waste reservoir, such that flow is not generated at the outlet.

25. The method of claim 18, wherein the drug supply reservoir comprises a reservoir channel of greater length than a length of the delivery channel.

26. The method of claim 25, wherein the reservoir channel length is greater than both a width and a height of the reservoir channel.

27. The method of claim 18 wherein loading the drug from the drug supply reservoir into the delivery channel while producing substantially negligible flow at the outlet of the delivery channel comprises:
   activating the dosing pump to drive the drug from the drug supply reservoir into the delivery channel and to pull at least a portion of the carrier fluid out from the delivery channel and into the drug supply reservoir; and
   deactivating the dosing pump after delivering a predetermined amount of the drug into the delivery channel.

28. The method of claim 27, wherein a volume of drug driven into the delivery channel is substantially equal to a volume of the carrier fluid pulled into the drug supply reservoir.

29. The method of claim 27, wherein the dosing pump drives drug in only one direction.

30. The method of claim 27, wherein the dosing pump delivers at least 200 nL per stroke.

31. The method of claim 27, wherein the dosing pump is deactivated after a single stroke.

* * * * *